United States Patent [19]

Gluchowski et al.

[11] Patent Number: 5,578,611

[45] Date of Patent: Nov. 26, 1996

[54] USE OF α-1C SPECIFIC COMPOUNDS TO TREAT BENIGN PROSTATIC HYPERPLASIA

[75] Inventors: Charles Gluchowski, Wayne; Carlos C. Forray, Paramus; George Chiu, Bridgewater; Theresa A. Branchek, Teaneck; John M. Wetzel, Elmwood Park; Paul R. Hartig, Kinnelon, all of N.J.

[73] Assignee: Synaptic Pharmaceutical Corporation, Paramus, N.J.

[*] Notice: The term of this patent shall not extend beyond the expiration date of Pat. No. 5,403,847.

[21] Appl. No.: 228,932

[22] Filed: Apr. 13, 1994

Related U.S. Application Data

[63] Continuation-in-part of Ser. No. 975,867, Nov. 13, 1992, Pat. No. 5,403,847, and a continuation-in-part of PCT/US93/10950, Nov. 12, 1993.

[51] Int. Cl.$^6$ ..................... A61K 31/445; A61K 31/135
[52] U.S. Cl. ............................. 514/318; 514/654
[58] Field of Search ..................... 514/318, 654

[56] References Cited

U.S. PATENT DOCUMENTS

| | | | |
|---|---|---|---|
| 4,975,440 | 12/1990 | Flockerzi et al. | 514/318 |
| 4,994,461 | 2/1991 | Ulrich | 514/252 |
| 5,403,847 | 4/1995 | Gluchowski et al. | 514/318 |

FOREIGN PATENT DOCUMENTS

| | | |
|---|---|---|
| 0176956 | 4/1986 | European Pat. Off. . |
| 3709796 | 11/1987 | Germany . |
| 9118599 | 12/1991 | WIPO . |
| 9421660 | 9/1994 | WIPO . |

OTHER PUBLICATIONS

Lomasney, J. W., et al., "molecular Cloning and Expression of the cDNA for the Alpha$_{1A}$-Adrenergic Receptor," Journal of Biological Chemistry, 266, 6365–6369 (1991).

Lepor, H., et al., "A Dose Titration Study Evaluating Terazosin, A Selective, Once–A–Day Alpha 1–Blocker for the Treatment of Symptomatic Benign Prostatic Hyperlasia," Journal of Urology, 144, 1393–1398 (1990).

Gup, D., et al., "Autonomic Receptors in Human Prostate Adenomas," Journal of Urology, 143, 179–185 (1990).

Lepor, H., et al., "The Effect of Electrocautery on Neurotransmitter Receptor Binding Assays in the Canine Prostate," Medline Abstracts, 88317114 (1988).

Lepor, H., et al., "The Alpha Adrenergic Binding Properties of Terazosin in the Human Prostate Adenoma and Canine Brain," Medline Abstracts, 88317113 (1988).

Ramarao, C. S., et al., "Genomic Organization and Expression of the Human Alpha$_{1B}$–Adrenergic Receptor," J. Biol. Chem., 267, 21936–21944 (1992).

I. Marshall, et al., Abstract No. C97 of an oral presentation given during a Sep. 9–11 Meeting of the British Pharmacological Society (1992).

Archibald, J. L., et al., "Antihypertensive Ureidopiperidines," Journal of Medicinal Chemistry, 23, 857–861 (1980).

Boer, R., et al., "(+)–Niguldipine binds with very high affinity to Ca$^{2+}$ channels and to a subtype of $\alpha$–adrenoreceptors," European Journal of Pharmacology—Molecular Pharmacology Section, 172, 131–145 (1989).

Forray, C., et al., "The $\alpha_1$–Adrenergic Receptor that Mediates Smooth Muscle Contraction in Human Prostate Has the Pharmacological Properties of Cloned Human $\alpha_{1C}$ Subtype," Molecular Pharmacology, 45, 703–708 (1994).

Forray, C., Chiu, G., et al., "Effects of Novel Alpha–1C Adrenergic Receptor Antagonists on the Contraction of Human Prostate Smooth Muscle", American Urological Association Eighty–ninth Annual Meeting, May 14–19, 1994, The Journal of Urology, Association Eighty–ninth Annual Meeting, May 14–19, 1994, The Journal of Urology, 151(5), Abstract #159 (May 1994).

Forray, C., Bard, J. A., et al., "Comparison of the Pharmacological Properties of the Cloned Bovine, Human, and Ray $\alpha_{1C}$–Adrenergic Receptors," The FASEB Journal, 8(4), Abstract #2042 (1994).

Gong, G., et al., "$\alpha_{1C}$–Adrenergic Antagonists and Orthostatic Hypotension in the Rat," The FASEB Journal, 8(4), Abstract #2043 (1994).

Lepor, H., et al., "Localization of Alpha$_{1C}$ Adrenoceptor ($\alpha_{1C}$ AR) Subtypes in the Human Prostate," American Urological Association Eighty–ninth Annual Meeting, May 14–19, 1994, The Journal of Urology, 151(15), Abstract #614 (May 1994).

Hieble, J. P., et al., "In vitro characterization of the $\alpha$hd 1–adrenoreceptors in human prostate," European Journal of Pharmacology, 107, 111–117 (1985).

Perez, J. L., et al., "Is the $\alpha_{1C}$–Adrenergic Receptor the $\alpha_{1A}$–Subtype?" The FASEB Journal, 8(4), Abstract #2041 (1994).

Tang, R., et al., "Localization of Alpha 1C Adrenoceptor ($\alpha$1C AR) Subtypes in the Human Prostatic Tissue," The FASEB Journal, 8(5), Abstract #5070 (1994).

Wetzel, J. M., et al., "Structural and Functional Studies of the Human $\alpha_{1C}$ Adrenergic Receptor: The Orientation of Transmembrane Helix 5," The FASEB Journal, 8(4) Abstract #2182 (1994).

Yamada, S., et al., "$\alpha_{1A}$–Adrenergic Receptors in Human Prostate: Characterization and Alteration in Benign Prostatic Hypertrophy," Journal of Pharmacology and Experimental Therapeutics, 242, 326–330 (1987).

Primary Examiner—Marianne M. Cintins
Assistant Examiner—William R. A. Jarvis
Attorney, Agent, or Firm—John P. White

[57] ABSTRACT

The subject invention provides a method of treating benign prostatic hyperplasia in a subject which comprises administering to the subject a therapeutically effective amount of a compound which binds to a human $\alpha_{1C}$ adrenergic receptor with a binding affinity greater than ten-fold higher than the binding affinity with which the compound binds to a human $\alpha_{1A}$ adrenergic receptor, a human $\alpha_{1B}$ adrenergic receptor, a human histamine H$_1$ receptor and $\alpha_2$ adrenergic receptor. The subject invention also provides a method of inhibiting contraction of prostate tissue which comprises contacting the prostate tissue with an effective contraction-inhibiting amount of such compound.

36 Claims, 2 Drawing Sheets

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 2140 base pairs
        ( B ) TYPE: nucleic acid
        ( C ) STRANDEDNESS: single
        ( D ) TOPOLOGY: unknown ( i i ) MOLECULE TYPE: DNA (genomic)

( i i i ) HYPOTHETICAL: N ( i v ) ANTI-SENSE: N ( i x ) FEATURE:
        ( A ) NAME/KEY: CDS
        ( B ) LOCATION: 178..1893
        ( D ) OTHER INFORMATION:

( x i ) SEQUENCE DESCRIPTION: SEQ ID NO:1:

```
CCGGGCCAGG  CACGTCCGCT  CTCGGACAGC  CGCTCCGCGT  CACAGGAACT  TGGGCAGGAC      60

CCGACGGGAC  CCGTGCGCGG  AGCTGCATCT  GGAGCCCCGC  GGCTATGCCC  TGTGCTCCCC     120

TCCTGCCGGC  CGCTCGTTCT  GTGCCCCCGG  CCCGGCCACC  GACGGCCGCG  CGTTGAG       177

ATG  ACT  TTC  CGC  GAT  CTC  CTG  AGC  GTC  AGT  TTC  GAG  GGA  CCC  CGC  CCG   225
Met  Thr  Phe  Arg  Asp  Leu  Leu  Ser  Val  Ser  Phe  Glu  Gly  Pro  Arg  Pro
 1              5                        10                       15

GAC  AGC  AGC  GCA  GGG  GGC  TCC  AGC  GCG  GGC  GGC  GGG  GGC  AGC  GCG         273
Asp  Ser  Ser  Ala  Gly  Gly  Ser  Ser  Ala  Gly  Gly  Gly  Gly  Ser  Ala
                20                       25                       30

GGC  GGC  GCG  GCC  CCC  TCG  GAG  GGC  CCG  GCG  GTG  GGC  GGC  GTG  CCG  GGG   321
Gly  Gly  Ala  Ala  Pro  Ser  Glu  Gly  Pro  Ala  Val  Gly  Gly  Val  Pro  Gly
            35                       40                       45

GGC  GCG  GGC  GGC  GGC  GGC  GGC  GTG  GTG  GGC  GCA  GGC  AGC  GGC  GAG  GAC   369
Gly  Ala  Gly  Gly  Gly  Gly  Gly  Val  Val  Gly  Ala  Gly  Ser  Gly  Glu  Asp
        50                       55                       60

AAC  CGG  AGC  TCC  GCG  GGG  GAG  CCG  GGG  AGC  GCG  GGC  GCG  GGC  GGC  GAC   417
Asn  Arg  Ser  Ser  Ala  Gly  Glu  Pro  Gly  Ser  Ala  Gly  Ala  Gly  Gly  Asp
65                       70                       75                       80

GTG  AAT  GGC  ACG  GCG  GCC  GTC  GGG  GGA  CTG  GTG  GTG  AGC  GCG  CAG  GGC   465
Val  Asn  Gly  Thr  Ala  Ala  Val  Gly  Gly  Leu  Val  Val  Ser  Ala  Gln  Gly
                 85                       90                       95

GTG  GGC  GTG  GGC  GTC  TTC  CTG  GCA  GCC  TTC  ATC  CTT  ATG  GCC  GTG  GCA   513
Val  Gly  Val  Gly  Val  Phe  Leu  Ala  Ala  Phe  Ile  Leu  Met  Ala  Val  Ala
                100                      105                      110

GGT  AAC  CTG  CTT  GTC  ATC  CTC  TCA  GTG  GCC  TGC  AAC  CGC  CAC  CTG  CAG   561
Gly  Asn  Leu  Leu  Val  Ile  Leu  Ser  Val  Ala  Cys  Asn  Arg  His  Leu  Gln
            115                      120                      125

ACC  GTC  ACC  AAC  TAT  TTC  ATC  GTG  AAC  CTG  GCC  GTG  GCC  GAC  CTG  CTG   609
Thr  Val  Thr  Asn  Tyr  Phe  Ile  Val  Asn  Leu  Ala  Val  Ala  Asp  Leu  Leu
        130                      135                      140

CTG  AGC  GCC  ACC  GTA  CTG  CCC  TTC  TCG  GCC  ACC  ATG  GAG  GTT  CTG  GGC   657
Leu  Ser  Ala  Thr  Val  Leu  Pro  Phe  Ser  Ala  Thr  Met  Glu  Val  Leu  Gly
145                      150                      155                      160

TTC  TGG  GCC  TTT  GGC  CGC  GCC  TTC  TGC  GAC  GTA  TGG  GCC  GCC  GTG  GAC   705
Phe  Trp  Ala  Phe  Gly  Arg  Ala  Phe  Cys  Asp  Val  Trp  Ala  Ala  Val  Asp
                165                      170                      175

GTG  CTG  TGC  TGC  ACG  GCC  TCC  ATC  CTC  AGC  CTC  TGC  ACC  ATC  TCC  GTG   753
```

|     |     |     |     |     |     |     |     |     |     |     |     |     |     |     |     |
|---|---|---|---|---|---|---|---|---|---|---|---|---|---|---|---|
| Val | Leu | Cys | Cys<br>180 | Thr | Ala | Ser | Ile | Leu<br>185 | Ser | Leu | Cys | Thr | Ile<br>190 | Ser | Val |
| GAC | CGG | TAC | GTG | GGC | GTG | CGC | CAC | TCA | CTC | AAG | TAC | CCA | GCC | ATC | ATG |
| Asp | Arg | Tyr<br>195 | Val | Gly | Val | Arg | His<br>200 | Ser | Leu | Lys | Tyr | Pro<br>205 | Ala | Ile | Met |
| ACC | GAG | CGC | AAG | GCG | GCC | GCC | ATC | CTG | GCC | CTG | CTC | TGG | GTC | GTA | GCC |
| Thr | Glu<br>210 | Arg | Lys | Ala | Ala<br>215 | Ala | Ile | Leu | Ala | Leu<br>220 | Leu | Trp | Val | Val | Ala |
| CTG | GTG | GTG | TCC | GTA | GGG | CCC | CTG | CTG | GGC | TGG | AAG | GAG | CCC | GTG | CCC |
| Leu<br>225 | Val | Val | Ser | Val | Gly<br>230 | Pro | Leu | Leu | Gly | Trp<br>235 | Lys | Glu | Pro | Val | Pro<br>240 |
| CCT | GAC | GAG | CGC | TTC | TGC | GGT | ATC | ACC | GAG | GAG | GCG | GGC | TAC | GCT | GTC |
| Pro | Asp | Glu | Arg | Phe<br>245 | Cys | Gly | Ile | Thr | Glu<br>250 | Glu | Ala | Gly | Tyr | Ala<br>255 | Val |
| TTC | TCC | TCC | GTG | TGC | TCC | TTC | TAC | CTG | CCC | ATG | GCG | GTC | ATC | GTG | GTC |
| Phe | Ser | Ser | Val<br>260 | Cys | Ser | Phe | Tyr | Leu<br>265 | Pro | Met | Ala | Val | Ile<br>270 | Val | Val |
| ATG | TAC | TGC | CGC | GTG | TAC | GTG | GTC | GCG | CGC | AGC | ACC | ACG | CGC | AGC | CTC |
| Met | Tyr | Cys<br>275 | Arg | Val | Tyr | Val<br>280 | Val | Ala | Arg | Ser | Thr<br>285 | Thr | Arg | Ser | Leu |
| GAG | GCA | GGC | GTC | AAG | CGC | GAG | CGA | GGC | AAG | GCC | TCC | GAG | GTG | GTG | CTG |
| Glu | Ala<br>290 | Gly | Val | Lys | Arg | Glu<br>295 | Arg | Gly | Lys | Ala | Ser<br>300 | Glu | Val | Val | Leu |
| CGC | ATC | CAC | TGT | CGC | GGC | GCG | GCC | ACG | GGC | GCC | GAC | GGG | GCG | CAC | GGC |
| Arg<br>305 | Ile | His | Cys | Arg | Gly<br>310 | Ala | Ala | Thr | Gly | Ala<br>315 | Asp | Gly | Ala | His | Gly<br>320 |
| ATG | CGC | AGC | GCC | AAG | GGC | CAC | ACC | TTC | CGC | AGC | TCG | CTC | TCC | GTG | CGC |
| Met | Arg | Ser | Ala | Lys<br>325 | Gly | His | Thr | Phe | Arg<br>330 | Ser | Ser | Leu | Ser | Val<br>335 | Arg |
| CTG | CTC | AAG | TTC | TCC | CGT | GAG | AAG | AAA | GCG | GCC | AAG | ACT | CTG | GCC | ATC |
| Leu | Leu | Lys | Phe<br>340 | Ser | Arg | Glu | Lys | Lys<br>345 | Ala | Ala | Lys | Thr | Leu<br>350 | Ala | Ile |
| GTC | GTG | GGT | GTC | TTC | GTG | CTC | TGC | TGG | TTC | CCT | TTC | TTC | TTT | GTC | CTG |
| Val | Val | Gly<br>355 | Val | Phe | Val | Leu | Cys<br>360 | Trp | Phe | Pro | Phe | Phe<br>365 | Phe | Val | Leu |
| CCG | CTC | GGC | TCC | TTG | TTC | CCG | CAG | CTG | AAG | CCA | TCG | GAG | GGC | GTC | TTC |
| Pro | Leu<br>370 | Gly | Ser | Leu | Phe | Pro<br>375 | Gln | Leu | Lys | Pro | Ser<br>380 | Glu | Gly | Val | Phe |
| AAG | GTC | ATC | TTC | TGG | CTC | GGC | TAC | TTC | AAC | AGC | TGC | GTG | AAC | CCG | CTC |
| Lys<br>385 | Val | Ile | Phe | Trp | Leu<br>390 | Gly | Tyr | Phe | Asn | Ser<br>395 | Cys | Val | Asn | Pro | Leu<br>400 |
| ATC | TAC | CCC | TGT | TCC | AGC | CGC | GAG | TTC | AAG | CGC | GCC | TTC | CTC | CGT | CTC |
| Ile | Tyr | Pro | Cys | Ser<br>405 | Ser | Arg | Glu | Phe | Lys<br>410 | Arg | Ala | Phe | Leu | Arg<br>415 | Leu |
| CTG | CGC | TGC | CAG | TGC | CGT | CGT | CGC | CGG | CGC | CGC | CCT | CTC | TGG | CGT |     |
| Leu | Arg | Cys | Gln<br>420 | Cys | Arg | Arg | Arg | Arg<br>425 | Arg | Arg | Pro | Leu | Trp<br>430 | Arg |     |
| GTC | TAC | GGC | CAC | CAC | TGG | CGG | GCC | TCC | ACC | AGC | GGC | CTG | CGC | CAG | GAC |
| Val | Tyr | Gly<br>435 | His | His | Trp | Arg<br>440 | Ala | Ser | Thr | Ser | Gly<br>445 | Leu | Arg | Gln | Asp |
| TGC | GCC | CCG | AGT | TCG | GGC | GAC | GCG | CCC | CCC | GGA | GCG | CCG | CTG | GCC | CTC |
| Cys | Ala | Pro<br>450 | Ser | Ser | Gly | Asp<br>455 | Ala | Pro | Pro | Gly | Ala<br>460 | Pro | Leu | Ala | Leu |
| ACC | GCG | CTC | CCC | GAC | CCC | GAC | CCC | GAA | CCC | CCA | GGC | ACG | CCC | GAG | ATG |
| Thr | Ala | Leu<br>465 | Pro | Asp | Pro<br>470 | Asp | Pro | Glu | Pro<br>475 | Pro | Gly | Thr | Pro | Glu<br>480 | Met |
| CAG | GCT | CCG | GTC | GCC | AGC | CGT | CGA | AAG | CCA | CCC | AGC | GCC | TTC | CGC | GAG |
| Gln | Ala | Pro<br>485 | Val | Ala | Ser | Arg<br>490 | Arg | Lys | Pro | Pro | Ser<br>495 | Ala | Phe | Arg | Glu |
| TGG | AGG | CTG | CTG | GGG | CCG | TTC | CGG | AGA | CCC | ACG | ACC | CAG | CTG | CGC | GCC |

801
849
897
945
993
1041
1089
1137
1185
1233
1281
1329
1377
1425
1473
1521
1569
1617
1665
1713

|  |  |  |  |  |  |  |  |  |  |  |  |  |  |  |  |
|---|---|---|---|---|---|---|---|---|---|---|---|---|---|---|---|
| Trp | Arg | Leu | Leu | Gly | Pro | Phe | Arg | Arg | Pro | Thr | Thr | Gln | Leu | Arg | Ala |
|  |  | 500 |  |  |  |  | 505 |  |  |  |  | 510 |  |  |  |

| AAA | GTC | TCC | AGC | CTG | TCG | CAC | AAG | ATC | CGC | GCC | GGG | GGC | GCG | CAG | CGC | 1761 |
|---|---|---|---|---|---|---|---|---|---|---|---|---|---|---|---|---|
| Lys | Val | Ser | Ser | Leu | Ser | His | Lys | Ile | Arg | Ala | Gly | Gly | Ala | Gln | Arg |  |
|  |  | 515 |  |  |  |  | 520 |  |  |  |  | 525 |  |  |  |  |

| GCA | GAG | GCA | GCG | TGC | GCC | CAG | CGC | TCA | GAG | GTG | GAG | GCT | GTG | TCC | CTA | 1809 |
|---|---|---|---|---|---|---|---|---|---|---|---|---|---|---|---|---|
| Ala | Glu | Ala | Ala | Cys | Ala | Gln | Arg | Ser | Glu | Val | Glu | Ala | Val | Ser | Leu |  |
|  |  | 530 |  |  |  |  | 535 |  |  |  |  | 540 |  |  |  |  |

| GGC | GTC | CCA | CAC | GAG | GTG | GCC | GAG | GGC | GCC | ACC | TGC | CAG | GCC | TAC | GAA | 1857 |
|---|---|---|---|---|---|---|---|---|---|---|---|---|---|---|---|---|
| Gly | Val | Pro | His | Glu | Val | Ala | Glu | Gly | Ala | Thr | Cys | Gln | Ala | Tyr | Glu |  |
| 545 |  |  |  |  | 550 |  |  |  |  | 555 |  |  |  |  | 560 |  |

| TTG | GCC | GAC | TAC | AGC | AAC | CTA | CGG | GAG | ACC | GAT | ATT | TAAGGACCCC |  |  | 1903 |
|---|---|---|---|---|---|---|---|---|---|---|---|---|---|---|---|
| Leu | Ala | Asp | Tyr | Ser | Asn | Leu | Arg | Glu | Thr | Asp | Ile |  |  |  |  |
|  |  |  |  | 565 |  |  |  |  | 570 |  |  |  |  |  |  |

| AGAGCTAGGC | CGCGGAGTGT | GCTGGGCTTG | GGGGTAAGGG | GGACCAGAGA | GGCGGGCTGG | 1963 |
|---|---|---|---|---|---|---|
| TGTTCTAAGA | GCCCCGTGC | AAATCGGAGA | CCCGGAAACT | GATCAGGGCA | GCTGCTCTGT | 2023 |
| GACATCCCTG | AGGAACTGGG | CAGAGCTTGA | GGCTGGAGCC | CTTGAAAGGT | GAAAAGTAGT | 2083 |
| GGGGCCCCCT | GCTGGACTCA | GGTGCCCAGA | ACTCTTTCT | TAGAAGGGAG | AGGCTGC | 2140 |

( 2 ) INFORMATION FOR SEQ ID NO:2:

( i ) SEQUENCE CHARACTERISTICS:
( A ) LENGTH: 572 amino acids
( B ) TYPE: amino acid
( D ) TOPOLOGY: linear ( i i ) MOLECULE TYPE: protein ( x i ) SEQUENCE DESCRIPTION: SEQ ID NO:2:

| Met | Thr | Phe | Arg | Asp | Leu | Leu | Ser | Val | Ser | Phe | Glu | Gly | Pro | Arg | Pro |
|---|---|---|---|---|---|---|---|---|---|---|---|---|---|---|---|
| 1 |  |  |  | 5 |  |  |  |  | 10 |  |  |  |  | 15 |  |
| Asp | Ser | Ser | Ala | Gly | Gly | Ser | Ser | Ala | Gly | Gly | Gly | Gly | Gly | Ser | Ala |
|  |  |  | 20 |  |  |  | 25 |  |  |  |  | 30 |  |  |  |
| Gly | Gly | Ala | Ala | Pro | Ser | Glu | Gly | Pro | Ala | Val | Gly | Gly | Val | Pro | Gly |
|  |  | 35 |  |  |  | 40 |  |  |  |  | 45 |  |  |  |  |
| Gly | Ala | Gly | Gly | Gly | Gly | Val | Val | Gly | Ala | Gly | Ser | Gly | Glu | Asp |  |
|  | 50 |  |  |  |  | 55 |  |  |  |  | 60 |  |  |  |  |
| Asn | Arg | Ser | Ser | Ala | Gly | Glu | Pro | Gly | Ser | Ala | Gly | Ala | Gly | Gly | Asp |
| 65 |  |  |  |  | 70 |  |  |  |  | 75 |  |  |  |  | 80 |
| Val | Asn | Gly | Thr | Ala | Ala | Val | Gly | Gly | Leu | Val | Val | Ser | Ala | Gln | Gly |
|  |  |  |  | 85 |  |  |  |  | 90 |  |  |  |  | 95 |  |
| Val | Gly | Val | Gly | Val | Phe | Leu | Ala | Ala | Phe | Ile | Leu | Met | Ala | Val | Ala |
|  |  |  | 100 |  |  |  | 105 |  |  |  |  | 110 |  |  |  |
| Gly | Asn | Leu | Leu | Val | Ile | Leu | Ser | Val | Ala | Cys | Asn | Arg | His | Leu | Gln |
|  |  | 115 |  |  |  | 120 |  |  |  |  | 125 |  |  |  |  |
| Thr | Val | Thr | Asn | Tyr | Phe | Ile | Val | Asn | Leu | Ala | Val | Ala | Asp | Leu | Leu |
|  | 130 |  |  |  |  | 135 |  |  |  |  | 140 |  |  |  |  |
| Leu | Ser | Ala | Thr | Val | Leu | Pro | Phe | Ser | Ala | Thr | Met | Glu | Val | Leu | Gly |
| 145 |  |  |  |  | 150 |  |  |  |  | 155 |  |  |  |  | 160 |
| Phe | Trp | Ala | Phe | Gly | Arg | Ala | Phe | Cys | Asp | Val | Trp | Ala | Ala | Val | Asp |
|  |  |  |  | 165 |  |  |  |  | 170 |  |  |  |  | 175 |  |
| Val | Leu | Cys | Cys | Thr | Ala | Ser | Ile | Leu | Ser | Leu | Cys | Thr | Ile | Ser | Val |
|  |  |  | 180 |  |  |  | 185 |  |  |  |  | 190 |  |  |  |
| Asp | Arg | Tyr | Val | Gly | Val | Arg | His | Ser | Leu | Lys | Tyr | Pro | Ala | Ile | Met |
|  |  | 195 |  |  |  | 200 |  |  |  |  | 205 |  |  |  |  |
| Thr | Glu | Arg | Lys | Ala | Ala | Ala | Ile | Leu | Ala | Leu | Leu | Trp | Val | Val | Ala |
|  | 210 |  |  |  |  | 215 |  |  |  |  | 220 |  |  |  |  |

```
Leu  Val  Val  Ser  Val  Gly  Pro  Leu  Leu  Gly  Trp  Lys  Glu  Pro  Val  Pro
225            230                      235                      240

Pro  Asp  Glu  Arg  Phe  Cys  Gly  Ile  Thr  Glu  Ala  Gly  Tyr  Ala  Val
                    245                 250                      255

Phe  Ser  Ser  Val  Cys  Ser  Phe  Tyr  Leu  Pro  Met  Ala  Val  Ile  Val  Val
               260                 265                      270

Met  Tyr  Cys  Arg  Val  Tyr  Val  Ala  Arg  Ser  Thr  Thr  Arg  Ser  Leu
          275                 280                      285

Glu  Ala  Gly  Val  Lys  Arg  Glu  Arg  Gly  Lys  Ala  Ser  Glu  Val  Val  Leu
     290                      295                 300

Arg  Ile  His  Cys  Arg  Gly  Ala  Ala  Thr  Gly  Ala  Asp  Gly  Ala  His  Gly
305                      310                 315                      320

Met  Arg  Ser  Ala  Lys  Gly  His  Thr  Phe  Arg  Ser  Ser  Leu  Ser  Val  Arg
                    325                      330                 335

Leu  Leu  Lys  Phe  Ser  Arg  Glu  Lys  Lys  Ala  Ala  Lys  Thr  Leu  Ala  Ile
               340                      345                 350

Val  Val  Gly  Val  Phe  Val  Leu  Cys  Trp  Phe  Pro  Phe  Phe  Val  Leu
          355                      360                 365

Pro  Leu  Gly  Ser  Leu  Phe  Pro  Gln  Leu  Lys  Pro  Ser  Glu  Gly  Val  Phe
370                      375                 380

Lys  Val  Ile  Phe  Trp  Leu  Gly  Tyr  Phe  Asn  Ser  Cys  Val  Asn  Pro  Leu
385                 390                 395                           400

Ile  Tyr  Pro  Cys  Ser  Ser  Arg  Glu  Phe  Lys  Arg  Ala  Phe  Leu  Arg  Leu
               405                      410                      415

Leu  Arg  Cys  Gln  Cys  Arg  Arg  Arg  Arg  Arg  Arg  Pro  Leu  Trp  Arg
               420                      425                 430

Val  Tyr  Gly  His  His  Trp  Arg  Ala  Ser  Thr  Ser  Gly  Leu  Arg  Gln  Asp
          435                      440                 445

Cys  Ala  Pro  Ser  Ser  Gly  Asp  Ala  Pro  Pro  Gly  Ala  Pro  Leu  Ala  Leu
     450                      455                 460

Thr  Ala  Leu  Pro  Asp  Pro  Asp  Pro  Glu  Pro  Pro  Gly  Thr  Pro  Glu  Met
465                      470                 475                      480

Gln  Ala  Pro  Val  Ala  Ser  Arg  Arg  Lys  Pro  Pro  Ser  Ala  Phe  Arg  Glu
                    485                 490                      495

Trp  Arg  Leu  Leu  Gly  Pro  Phe  Arg  Arg  Pro  Thr  Thr  Gln  Leu  Arg  Ala
               500                 505                      510

Lys  Val  Ser  Ser  Leu  Ser  His  Lys  Ile  Arg  Ala  Gly  Gly  Ala  Gln  Arg
          515                 520                      525

Ala  Glu  Ala  Ala  Cys  Ala  Gln  Arg  Ser  Glu  Val  Glu  Ala  Val  Ser  Leu
     530                 535                 540

Gly  Val  Pro  His  Glu  Val  Ala  Glu  Gly  Ala  Thr  Cys  Gln  Ala  Tyr  Glu
545                      550                 555                      560

Leu  Ala  Asp  Tyr  Ser  Asn  Leu  Arg  Glu  Thr  Asp  Ile
               565                      570
```

( 2 ) INFORMATION FOR SEQ ID NO:3:

( i ) SEQUENCE CHARACTERISTICS:
        ( A ) LENGTH: 1738 base pairs
        ( B ) TYPE: nucleic acid
        ( C ) STRANDEDNESS: single
        ( D ) TOPOLOGY: unknown ( i i ) MOLECULE TYPE: DNA (genomic)

( i i i ) HYPOTHETICAL: N ( i v ) ANTI-SENSE: N ( i x ) FEATURE:
    ( A ) NAME/KEY: CDS
    ( B ) LOCATION: 124..1683
    ( D ) OTHER INFORMATION:

( x i ) SEQUENCE DESCRIPTION: SEQ ID NO:3:

```
GCCAGGAGGG CGCCTCTGGG AAGAAGACCA CGGGGGAAGC AAAGTTTCAG GGCAGCTGAG      60

GAGCCTTCGC CGCAGCCCTT CCGAGCCCAA TCATCCCCCA GGCTATGGAG GGCGGACTCT     120

AAG ATG AAT CCC GAC CTG GAC ACC GGC CAC AAC ACA TCA GCA CCT GCC      168
    Met Asn Pro Asp Leu Asp Thr Gly His Asn Thr Ser Ala Pro Ala
    1               5                  10                  15

CAC TGG GGA GAG TTG AAA AAT GCC AAC TTC ACT GGC CCC AAC CAG ACC      216
His Trp Gly Glu Leu Lys Asn Ala Asn Phe Thr Gly Pro Asn Gln Thr
                20                  25                  30

TCG AGC AAC TCC ACA CTG CCC CAG CTG GAC ATC ACC AGG GCC ATC TCT      264
Ser Ser Asn Ser Thr Leu Pro Gln Leu Asp Ile Thr Arg Ala Ile Ser
                35                  40                  45

GTG GGC CTG GTG CTG GGC GCC TTC ATC CTC TTT GCC ATC GTG GGC AAC      312
Val Gly Leu Val Leu Gly Ala Phe Ile Leu Phe Ala Ile Val Gly Asn
            50                  55                  60

ATC CTA GTC ATC TTG TCT GTG GCC TGC AAC CGG CAC CTG CGG ACG CCC      360
Ile Leu Val Ile Leu Ser Val Ala Cys Asn Arg His Leu Arg Thr Pro
        65                  70                  75

ACC AAC TAC TTC ATT GTC AAC CTG GCC ATG GCC GAC CTG CTG TTG AGC      408
Thr Asn Tyr Phe Ile Val Asn Leu Ala Met Ala Asp Leu Leu Leu Ser
80                  85                  90                  95

TTC ACC GTC CTG CCC TTC TCA GCG GCC CTA GAG GTG CTC GGC TAC TGG      456
Phe Thr Val Leu Pro Phe Ser Ala Ala Leu Glu Val Leu Gly Tyr Trp
                100                 105                 110

GTG CTG GGG CGG ATC TTC TGT GAC ATC TGG GCA GCC GTG GAT GTC CTG      504
Val Leu Gly Arg Ile Phe Cys Asp Ile Trp Ala Ala Val Asp Val Leu
                115                 120                 125

TGC TGC ACA GCG TCC ATT CTG AGC CTG TGC GCC ATC TCC ATC GAT CGC      552
Cys Cys Thr Ala Ser Ile Leu Ser Leu Cys Ala Ile Ser Ile Asp Arg
            130                 135                 140

TAC ATC GGG GTG CGC TAC TCT CTG CAG TAT CCC ACG CTG GTC ACC CGG      600
Tyr Ile Gly Val Arg Tyr Ser Leu Gln Tyr Pro Thr Leu Val Thr Arg
        145                 150                 155

AGG AAG GCC ATC TTG GCG CTG CTC AGT GTC TGG GTC TTG TCC ACC GTC      648
Arg Lys Ala Ile Leu Ala Leu Leu Ser Val Trp Val Leu Ser Thr Val
160                 165                 170                 175

ATC TCC ATC GGG CCT CTC CTT GGG TGG AAG GAG CCG GCA CCC AAC GAT      696
Ile Ser Ile Gly Pro Leu Leu Gly Trp Lys Glu Pro Ala Pro Asn Asp
                180                 185                 190

GAC AAG GAG TGC GGG GTC ACC GAA GAA CCC TTC TAT GCC CTC TTC TCC      744
Asp Lys Glu Cys Gly Val Thr Glu Glu Pro Phe Tyr Ala Leu Phe Ser
                195                 200                 205

TCT CTG GGC TCC TTC TAC ATC CCT CTG GCG GTC ATT CTA GTC ATG TAC      792
Ser Leu Gly Ser Phe Tyr Ile Pro Leu Ala Val Ile Leu Val Met Tyr
            210                 215                 220

TGC CGT GTC TAT ATA GTG GCC AAG AGA ACC ACC AAG AAC CTA GAG GCA      840
Cys Arg Val Tyr Ile Val Ala Lys Arg Thr Thr Lys Asn Leu Glu Ala
        225                 230                 235

GGA GTC ATG AAG GAG ATG TCC AAC TCC AAG GAG CTG ACC CTG AGG ATC      888
Gly Val Met Lys Glu Met Ser Asn Ser Lys Glu Leu Thr Leu Arg Ile
240                 245                 250                 255

CAT TCC AAG AAC TTT CAC GAG GAC ACC CTT AGC AGT ACC AAG GCC AAG      936
His Ser Lys Asn Phe His Glu Asp Thr Leu Ser Ser Thr Lys Ala Lys
                260                 265                 270
```

```
GGC CAC AAC CCC AGG AGT TCC ATA GCT GTC AAA CTT TTT AAG TTC TCC    984
Gly His Asn Pro Arg Ser Ser Ile Ala Val Lys Leu Phe Lys Phe Ser
            275             280             285

AGG GAA AAG AAA GCA GCT AAG ACG TTG GGC ATT GTG GTC GGT ATG TTC   1032
Arg Glu Lys Lys Ala Ala Lys Thr Leu Gly Ile Val Val Gly Met Phe
        290             295             300

ATC TTG TGC TGG CTA CCC TTC TTC ATC GCT CTA CCG CTT GGC TCC TTG   1080
Ile Leu Cys Trp Leu Pro Phe Phe Ile Ala Leu Pro Leu Gly Ser Leu
    305             310             315

TTC TCC ACC CTG AAG CCC CCC GAC GCC GTG TTC AAG GTG GTG TTC TGG   1128
Phe Ser Thr Leu Lys Pro Pro Asp Ala Val Phe Lys Val Val Phe Trp
320             325             330             335

CTG GGC TAC TTC AAC AGC TGC CTC AAC CCC ATC ATC TAC CCA TGC TCC   1176
Leu Gly Tyr Phe Asn Ser Cys Leu Asn Pro Ile Ile Tyr Pro Cys Ser
                340             345             350

AGC AAG GAG TTC AAG CGC GCT TTC GTG CGC ATC CTC GGG TGC CAG TGC   1224
Ser Lys Glu Phe Lys Arg Ala Phe Val Arg Ile Leu Gly Cys Gln Cys
            355             360             365

CGC GGC CGC GGC CGC CGC CGA CGC CGC CGC CGT CGC CTG GGC GGC       1272
Arg Gly Arg Gly Arg Arg Arg Arg Arg Arg Arg Arg Leu Gly Gly
        370             375             380

TGC GCC TAC ACC TAC CGG CCG TGG ACG CGC GGC GGC TCG CTG GAG CGC   1320
Cys Ala Tyr Thr Tyr Arg Pro Trp Thr Arg Gly Gly Ser Leu Glu Arg
    385             390             395

TCG CAG TCG CGC AAG GAC TCG CTG GAC GAC AGC GGC AGC TGC CTG AGC   1368
Ser Gln Ser Arg Lys Asp Ser Leu Asp Asp Ser Gly Ser Cys Leu Ser
400             405             410             415

GGC AGC CAG CGG ACC CTG CCC TCG GCC TCG CCG AGC CCG GGC TAC CTG   1416
Gly Ser Gln Arg Thr Leu Pro Ser Ala Ser Pro Ser Pro Gly Tyr Leu
                420             425             430

GGC CGC GGC GCG CCA CCG CCA GTC GAG CTG TGC GCC TTC CCC GAG TGG   1464
Gly Arg Gly Ala Pro Pro Pro Val Glu Leu Cys Ala Phe Pro Glu Trp
            435             440             445

AAG GCG CCC GGC GCC CTC CTG AGC CTG CCC GCG CCT GAG CCC CCC GGC   1512
Lys Ala Pro Gly Ala Leu Leu Ser Leu Pro Ala Pro Glu Pro Pro Gly
        450             455             460

CGC CGC GGC CGC CAC GAC TCG GGC CCG CTC TTC ACC TTC AAG CTC CTG   1560
Arg Arg Gly Arg His Asp Ser Gly Pro Leu Phe Thr Phe Lys Leu Leu
    465             470             475

ACC GAG CCC GAG AGC CCC GGG ACC GAC GGC GGC GCC AGC AAC GGA GGC   1608
Thr Glu Pro Glu Ser Pro Gly Thr Asp Gly Gly Ala Ser Asn Gly Gly
480             485             490             495

TGC GAG GCC GCG GCC GAC GTG GCC AAC GGG CAG CCG GGC TTC AAA AGC   1656
Cys Glu Ala Ala Ala Asp Val Ala Asn Gly Gln Pro Gly Phe Lys Ser
                500             505             510

AAC ATG CCC CTG GCG CCC GGG CAG TTT TAGGGCCCCC GTGCGCAGCT         1703
Asn Met Pro Leu Ala Pro Gly Gln Phe
            515             520

TTCTTTCCCT GGGGAGGAAA ACATCGTGGG GGGGA                            1738
```

( 2 ) INFORMATION FOR SEQ ID NO:4:

( i ) SEQUENCE CHARACTERISTICS:
        ( A ) LENGTH: 520 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

Met Asn Pro Asp Leu Asp Thr Gly His Asn Thr Ser Ala Pro Ala His

```
  1                    5                          10                         15

Trp  Gly  Glu  Leu  Lys  Asn  Ala  Asn  Phe  Thr  Gly  Pro  Asn  Gln  Thr  Ser
               20                       25                      30

Ser  Asn  Ser  Thr  Leu  Pro  Gln  Leu  Asp  Ile  Thr  Arg  Ala  Ile  Ser  Val
               35                       40                      45

Gly  Leu  Val  Leu  Gly  Ala  Phe  Ile  Leu  Phe  Ala  Ile  Val  Gly  Asn  Ile
          50                       55                      60

Leu  Val  Ile  Leu  Ser  Val  Ala  Cys  Asn  Arg  His  Leu  Arg  Thr  Pro  Thr
65                            70                  75                           80

Asn  Tyr  Phe  Ile  Val  Asn  Leu  Ala  Met  Ala  Asp  Leu  Leu  Leu  Ser  Phe
                    85                       90                           95

Thr  Val  Leu  Pro  Phe  Ser  Ala  Ala  Leu  Glu  Val  Leu  Gly  Tyr  Trp  Val
               100                      105                     110

Leu  Gly  Arg  Ile  Phe  Cys  Asp  Ile  Trp  Ala  Ala  Val  Asp  Val  Leu  Cys
               115                      120                     125

Cys  Thr  Ala  Ser  Ile  Leu  Ser  Leu  Cys  Ala  Ile  Ser  Ile  Asp  Arg  Tyr
          130                      135                      140

Ile  Gly  Val  Arg  Tyr  Ser  Leu  Gln  Tyr  Pro  Thr  Leu  Val  Thr  Arg  Arg
145                      150                      155                          160

Lys  Ala  Ile  Leu  Ala  Leu  Leu  Ser  Val  Trp  Val  Leu  Ser  Thr  Val  Ile
                    165                      170                     175

Ser  Ile  Gly  Pro  Leu  Leu  Gly  Trp  Lys  Glu  Pro  Ala  Pro  Asn  Asp  Asp
               180                      185                     190

Lys  Glu  Cys  Gly  Val  Thr  Glu  Glu  Pro  Phe  Tyr  Ala  Leu  Phe  Ser  Ser
          195                      200                      205

Leu  Gly  Ser  Phe  Tyr  Ile  Pro  Leu  Ala  Val  Ile  Leu  Val  Met  Tyr  Cys
          210                      215                      220

Arg  Val  Tyr  Ile  Val  Ala  Lys  Arg  Thr  Thr  Lys  Asn  Leu  Glu  Ala  Gly
225                      230                      235                          240

Val  Met  Lys  Glu  Met  Ser  Asn  Ser  Lys  Glu  Leu  Thr  Leu  Arg  Ile  His
                    245                      250                     255

Ser  Lys  Asn  Phe  His  Glu  Asp  Thr  Leu  Ser  Ser  Thr  Lys  Ala  Lys  Gly
               260                      265                     270

His  Asn  Pro  Arg  Ser  Ser  Ile  Ala  Val  Lys  Leu  Phe  Lys  Phe  Ser  Arg
          275                      280                      285

Glu  Lys  Lys  Ala  Ala  Lys  Thr  Leu  Gly  Ile  Val  Val  Gly  Met  Phe  Ile
     290                      295                      300

Leu  Cys  Trp  Leu  Pro  Phe  Phe  Ile  Ala  Leu  Pro  Leu  Gly  Ser  Leu  Phe
305                      310                      315                          320

Ser  Thr  Leu  Lys  Pro  Pro  Asp  Ala  Val  Phe  Lys  Val  Val  Phe  Trp  Leu
               325                      330                     335

Gly  Tyr  Phe  Asn  Ser  Cys  Leu  Asn  Pro  Ile  Ile  Tyr  Pro  Cys  Ser  Ser
               340                      345                     350

Lys  Glu  Phe  Lys  Arg  Ala  Phe  Val  Arg  Ile  Leu  Gly  Cys  Gln  Cys  Arg
          355                      360                      365

Gly  Arg  Gly  Arg  Arg  Arg  Arg  Arg  Arg  Arg  Arg  Leu  Gly  Gly  Cys
          370                      375                      380

Ala  Tyr  Thr  Tyr  Arg  Pro  Trp  Thr  Arg  Gly  Gly  Ser  Leu  Glu  Arg  Ser
385                      390                      395                          400

Gln  Ser  Arg  Lys  Asp  Ser  Leu  Asp  Asp  Ser  Gly  Ser  Cys  Leu  Ser  Gly
                    405                      410                     415

Ser  Gln  Arg  Thr  Leu  Pro  Ser  Ala  Ser  Pro  Ser  Pro  Gly  Tyr  Leu  Gly
               420                      425                     430
```

```
Arg Gly Ala Pro Pro Pro Val Glu Leu Cys Ala Phe Pro Glu Trp Lys
        435             440                 445
Ala Pro Gly Ala Leu Leu Ser Leu Pro Ala Pro Glu Pro Pro Gly Arg
        450             455             460
Arg Gly Arg His Asp Ser Gly Pro Leu Phe Thr Phe Lys Leu Leu Thr
465             470             475                         480
Glu Pro Glu Ser Pro Gly Thr Asp Gly Gly Ala Ser Asn Gly Gly Cys
                485             490                 495
Glu Ala Ala Ala Asp Val Ala Asn Gly Gln Pro Gly Phe Lys Ser Asn
        500                 505             510
Met Pro Leu Ala Pro Gly Gln Phe
        515             520
```

( 2 ) INFORMATION FOR SEQ ID NO:5:

( i ) SEQUENCE CHARACTERISTICS:
( A ) LENGTH: 1639 base pairs
( B ) TYPE: nucleic acid
( C ) STRANDEDNESS: single
( D ) TOPOLOGY: unknown ( i i ) MOLECULE TYPE: DNA (genomic)

( i i i ) HYPOTHETICAL: N ( i v ) ANTI-SENSE: N ( i x ) FEATURE:
( A ) NAME/KEY: CDS
( B ) LOCATION: 126..1523
( D ) OTHER INFORMATION:

( x i ) SEQUENCE DESCRIPTION: SEQ ID NO:5:

```
CCAGCCAAAC CACTGGCAGG CTCCCTCCAG CCGAGACCTT TTATTCCCGG CTCCCGAGCT    60

CCGCCTCCGC GCCAGCCCGG GAGGTGGCCC TGACAGCCGG ACCTCGCCCG GCCCCGGCTG   120

GGACC ATG GTG TTT CTC TCG GGA AAT GCT TCC GAC AGC TCC AAC TGC       167
      Met Val Phe Leu Ser Gly Asn Ala Ser Asp Ser Ser Asn Cys
       1               5                  10

ACC CAA CCG CCG GCA CCG GTG AAC ATT TCC AAG GCC ATT CTG CTC GGG     215
Thr Gln Pro Pro Ala Pro Val Asn Ile Ser Lys Ala Ile Leu Leu Gly
 15              20                  25                      30

GTG ATC TTG GGG GGC CTC ATT CTT TTC GGG GTG CTG GGT AAC ATC CTA     263
Val Ile Leu Gly Gly Leu Ile Leu Phe Gly Val Leu Gly Asn Ile Leu
             35                  40                  45

GTG ATC CTC TCC GTA GCC TGT CAC CGA CAC CTG CAC TCA GTC ACG CAC     311
Val Ile Leu Ser Val Ala Cys His Arg His Leu His Ser Val Thr His
             50                  55                  60

TAC TAC ATC GTC AAC CTG GCG GTG GCC GAC CTC CTG CTC ACC TCC ACG     359
Tyr Tyr Ile Val Asn Leu Ala Val Ala Asp Leu Leu Leu Thr Ser Thr
             65                  70                  75

GTG CTG CCC TTC TCC GCC ATC TTC GAG GTC CTA GGC TAC TGG GCC TTC     407
Val Leu Pro Phe Ser Ala Ile Phe Glu Val Leu Gly Tyr Trp Ala Phe
         80                  85                  90

GGC AGG GTC TTC TGC AAC ATC TGG GCG GCA GTG GAT GTG CTG TGC TGC     455
Gly Arg Val Phe Cys Asn Ile Trp Ala Ala Val Asp Val Leu Cys Cys
 95              100                 105                     110

ACC GCG TCC ATC ATG GGC CTC TGC ATC ATC TCC ATC GAC CGC TAC ATC     503
Thr Ala Ser Ile Met Gly Leu Cys Ile Ile Ser Ile Asp Arg Tyr Ile
             115                 120                 125

GGC GTG AGC TAC CCG CTG CGC TAC CCA ACC ATC GTC ACC CAG AGG AGG     551
Gly Val Ser Tyr Pro Leu Arg Tyr Pro Thr Ile Val Thr Gln Arg Arg
         130                 135                 140
```

| | | | | | | | | | | | | | | | | |
|---|---|---|---|---|---|---|---|---|---|---|---|---|---|---|---|---|
| GGT | CTC | ATG | GCT | CTG | CTC | TGC | GTC | TGG | GCA | CTC | TCC | CTG | GTC | ATA | TCC | 599 |
| Gly | Leu | Met | Ala | Leu | Leu | Cys | Val | Trp | Ala | Leu | Ser | Leu | Val | Ile | Ser | |
| | | 145 | | | | | 150 | | | | | 155 | | | | |
| ATT | GGA | CCC | CTG | TTC | GGC | TGG | AGG | CAG | CCG | GCC | CCC | GAG | GAC | GAG | ACC | 647 |
| Ile | Gly | Pro | Leu | Phe | Gly | Trp | Arg | Gln | Pro | Ala | Pro | Glu | Asp | Glu | Thr | |
| | 160 | | | | | 165 | | | | | 170 | | | | | |
| ATC | TGC | CAG | ATC | AAC | GAG | GAG | CCG | GGC | TAC | GTG | CTC | TTC | TCA | GCG | CTG | 695 |
| Ile | Cys | Gln | Ile | Asn | Glu | Glu | Pro | Gly | Tyr | Val | Leu | Phe | Ser | Ala | Leu | |
| 175 | | | | | 180 | | | | | 185 | | | | | 190 | |
| GGC | TCC | TTC | TAC | CTG | CCT | CTG | GCC | ATC | ATC | CTG | GTC | ATG | TAC | TGC | CGC | 743 |
| Gly | Ser | Phe | Tyr | Leu | Pro | Leu | Ala | Ile | Ile | Leu | Val | Met | Tyr | Cys | Arg | |
| | | | | 195 | | | | | 200 | | | | | 205 | | |
| GTC | TAC | GTG | GTG | GCC | AAG | AGG | GAG | AGC | CGG | GGC | CTC | AAG | TCT | GGC | CTC | 791 |
| Val | Tyr | Val | Val | Ala | Lys | Arg | Glu | Ser | Arg | Gly | Leu | Lys | Ser | Gly | Leu | |
| | | | 210 | | | | | 215 | | | | | 220 | | | |
| AAG | ACC | GAC | AAG | TCG | GAC | TCG | GAG | CAA | GTG | ACG | CTC | CGC | ATC | CAT | CGG | 839 |
| Lys | Thr | Asp | Lys | Ser | Asp | Ser | Glu | Gln | Val | Thr | Leu | Arg | Ile | His | Arg | |
| | | | 225 | | | | | 230 | | | | | 235 | | | |
| AAA | AAC | GCC | CCG | GCA | GGA | GGC | AGC | GGG | ATG | GCC | AGC | GCC | AAG | ACC | AAG | 887 |
| Lys | Asn | Ala | Pro | Ala | Gly | Gly | Ser | Gly | Met | Ala | Ser | Ala | Lys | Thr | Lys | |
| | | 240 | | | | | 245 | | | | | 250 | | | | |
| ACG | CAC | TTC | TCA | GTG | AGG | CTC | CTC | AAG | TTC | TCC | CGG | GAG | AAG | AAA | GCG | 935 |
| Thr | His | Phe | Ser | Val | Arg | Leu | Leu | Lys | Phe | Ser | Arg | Glu | Lys | Lys | Ala | |
| 255 | | | | | 260 | | | | | 265 | | | | | 270 | |
| GCC | AAA | ACG | CTG | GGC | ATC | GTG | GTC | GGC | TGC | TTC | GTC | CTC | TGC | TGG | CTG | 983 |
| Ala | Lys | Thr | Leu | Gly | Ile | Val | Val | Gly | Cys | Phe | Val | Leu | Cys | Trp | Leu | |
| | | | | 275 | | | | | 280 | | | | | 285 | | |
| CCT | TTT | TTC | TTA | GTC | ATG | CCC | ATT | GGG | TCT | TTC | TTC | CCT | GAT | TTC | AAG | 1031 |
| Pro | Phe | Phe | Leu | Val | Met | Pro | Ile | Gly | Ser | Phe | Phe | Pro | Asp | Phe | Lys | |
| | | | | 290 | | | | | 295 | | | | | 300 | | |
| CCC | TCT | GAA | ACA | GTT | TTT | AAA | ATA | GTA | TTT | TGG | CTC | GGA | TAT | CTA | AAC | 1079 |
| Pro | Ser | Glu | Thr | Val | Phe | Lys | Ile | Val | Phe | Trp | Leu | Gly | Tyr | Leu | Asn | |
| | | 305 | | | | | 310 | | | | | 315 | | | | |
| AGC | TGC | ATC | AAC | CCC | ATC | ATA | TAC | CCA | TGC | TCC | AGC | CAA | GAG | TTC | AAA | 1127 |
| Ser | Cys | Ile | Asn | Pro | Ile | Ile | Tyr | Pro | Cys | Ser | Ser | Gln | Glu | Phe | Lys | |
| | 320 | | | | | 325 | | | | | 330 | | | | | |
| AAG | GCC | TTT | CAG | AAT | GTC | TTG | AGA | ATC | CAG | TGT | CTC | TGC | AGA | AAG | CAG | 1175 |
| Lys | Ala | Phe | Gln | Asn | Val | Leu | Arg | Ile | Gln | Cys | Leu | Cys | Arg | Lys | Gln | |
| 335 | | | | | 340 | | | | | 345 | | | | | 350 | |
| TCT | TCC | AAA | CAT | GCC | CTG | GGC | TAC | ACC | CTG | CAC | CCG | CCC | AGC | CAG | GCC | 1223 |
| Ser | Ser | Lys | His | Ala | Leu | Gly | Tyr | Thr | Leu | His | Pro | Pro | Ser | Gln | Ala | |
| | | | | 355 | | | | | 360 | | | | | 365 | | |
| GTG | GAA | GGG | CAA | CAC | AAG | GAC | ATG | GTG | CGC | ATC | CCC | GTG | GGA | TCA | AGA | 1271 |
| Val | Glu | Gly | Gln | His | Lys | Asp | Met | Val | Arg | Ile | Pro | Val | Gly | Ser | Arg | |
| | | | 370 | | | | | 375 | | | | | 380 | | | |
| GAG | ACC | TTC | TAC | AGG | ATC | TCC | AAG | ACG | GAT | GGC | GTT | TGT | GAA | TGG | AAA | 1319 |
| Glu | Thr | Phe | Tyr | Arg | Ile | Ser | Lys | Thr | Asp | Gly | Val | Cys | Glu | Trp | Lys | |
| | | | 385 | | | | | 390 | | | | | 395 | | | |
| TTT | TTC | TCT | TCC | ATG | CCC | CGT | GGA | TCT | GCC | AGG | ATT | ACA | GTG | TCC | AAA | 1367 |
| Phe | Phe | Ser | Ser | Met | Pro | Arg | Gly | Ser | Ala | Arg | Ile | Thr | Val | Ser | Lys | |
| | | 400 | | | | | 405 | | | | | 410 | | | | |
| GAC | CAA | TCC | TCC | TGT | ACC | ACA | GCC | CGG | GTG | AGA | AGT | AAA | AGC | TTT | TTG | 1415 |
| Asp | Gln | Ser | Ser | Cys | Thr | Thr | Ala | Arg | Val | Arg | Ser | Lys | Ser | Phe | Leu | |
| 415 | | | | | 420 | | | | | 425 | | | | | 430 | |
| CAG | GTC | TGC | TGC | TGT | GTA | GGG | CCC | TCA | ACC | CCC | AGC | CTT | GAC | AAG | AAC | 1463 |
| Gln | Val | Cys | Cys | Cys | Val | Gly | Pro | Ser | Thr | Pro | Ser | Leu | Asp | Lys | Asn | |
| | | | | 435 | | | | | 440 | | | | | 445 | | |
| CAT | CAA | GTT | CCA | ACC | ATT | AAG | GTC | CAC | ACC | ATC | TCC | CTC | AGT | GAG | AAC | 1511 |
| His | Gln | Val | Pro | Thr | Ile | Lys | Val | His | Thr | Ile | Ser | Leu | Ser | Glu | Asn | |
| | | | 450 | | | | | 455 | | | | | 460 | | | |

```
GGG GAG GAA GTC TAGGACAGGA AAGATGCAGA GGAAAGGGGA ATATCTTAGG          1563
Gly Glu Glu Val
        465

TACCATACCC TGGAGTTCTA GAGGATTCCT CGACAAGCTT ATTCCGATCC AGACATGATA    1623

GATACATTGA TGAGTT                                                    1639
```

( 2 ) INFORMATION FOR SEQ ID NO:6:

( i ) SEQUENCE CHARACTERISTICS:
        ( A ) LENGTH: 466 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met Val Phe Leu Ser Gly Asn Ala Ser Asp Ser Ser Asn Cys Thr Gln
 1               5                  10                   15

Pro Pro Ala Pro Val Asn Ile Ser Lys Ala Ile Leu Leu Gly Val Ile
            20                  25                  30

Leu Gly Gly Leu Ile Leu Phe Gly Val Leu Gly Asn Ile Leu Val Ile
        35                  40                  45

Leu Ser Val Ala Cys His Arg His Leu His Ser Val Thr His Tyr Tyr
    50                  55                  60

Ile Val Asn Leu Ala Val Ala Asp Leu Leu Thr Ser Thr Val Leu
65                  70                  75                   80

Pro Phe Ser Ala Ile Phe Glu Val Leu Gly Tyr Trp Ala Phe Gly Arg
                85                  90                  95

Val Phe Cys Asn Ile Trp Ala Ala Val Asp Val Leu Cys Cys Thr Ala
            100                 105                 110

Ser Ile Met Gly Leu Cys Ile Ile Ser Ile Asp Arg Tyr Ile Gly Val
        115                 120                 125

Ser Tyr Pro Leu Arg Tyr Pro Thr Ile Val Thr Gln Arg Arg Gly Leu
    130                 135                 140

Met Ala Leu Leu Cys Val Trp Ala Leu Ser Leu Val Ile Ser Ile Gly
145                 150                 155                 160

Pro Leu Phe Gly Trp Arg Gln Pro Ala Pro Glu Asp Glu Thr Ile Cys
                165                 170                 175

Gln Ile Asn Glu Glu Pro Gly Tyr Val Leu Phe Ser Ala Leu Gly Ser
            180                 185                 190

Phe Tyr Leu Pro Leu Ala Ile Ile Leu Val Met Tyr Cys Arg Val Tyr
        195                 200                 205

Val Val Ala Lys Arg Glu Ser Arg Gly Leu Lys Ser Gly Leu Lys Thr
    210                 215                 220

Asp Lys Ser Asp Ser Glu Gln Val Thr Leu Arg Ile His Arg Lys Asn
225                 230                 235                 240

Ala Pro Ala Gly Gly Ser Gly Met Ala Ser Ala Lys Thr Lys Thr His
                245                 250                 255

Phe Ser Val Arg Leu Leu Lys Phe Ser Arg Glu Lys Lys Ala Ala Lys
            260                 265                 270

Thr Leu Gly Ile Val Val Gly Cys Phe Val Leu Cys Trp Leu Pro Phe
        275                 280                 285

Phe Leu Val Met Pro Ile Gly Ser Phe Phe Pro Asp Phe Lys Pro Ser
    290                 295                 300

Glu Thr Val Phe Lys Ile Val Phe Trp Leu Gly Tyr Leu Asn Ser Cys
305                 310                 315                 320
```

| | | | | | | | | | | | | | |
|---|---|---|---|---|---|---|---|---|---|---|---|---|---|
| Ile | Asn | Pro | Ile | Ile 325 | Tyr | Pro | Cys | Ser | Ser 330 | Gln | Glu | Phe | Lys | Lys 335 | Ala |
| Phe | Gln | Asn | Val 340 | Leu | Arg | Ile | Gln | Cys 345 | Leu | Cys | Arg | Lys | Gln 350 | Ser | Ser |
| Lys | His | Ala 355 | Leu | Gly | Tyr | Thr | Leu 360 | His | Pro | Pro | Ser | Gln 365 | Ala | Val | Glu |
| Gly | Gln 370 | His | Lys | Asp | Met | Val 375 | Arg | Ile | Pro | Val | Gly 380 | Ser | Arg | Glu | Thr |
| Phe 385 | Tyr | Arg | Ile | Ser | Lys 390 | Thr | Asp | Gly | Val | Cys 395 | Glu | Trp | Lys | Phe | Phe 400 |
| Ser | Ser | Met | Pro | Arg 405 | Gly | Ser | Ala | Arg | Ile 410 | Thr | Val | Ser | Lys | Asp 415 | Gln |
| Ser | Ser | Cys | Thr 420 | Thr | Ala | Arg | Val | Arg 425 | Ser | Lys | Ser | Phe | Leu 430 | Gln | Val |
| Cys | Cys | Cys 435 | Val | Gly | Pro | Ser | Thr 440 | Pro | Ser | Leu | Asp | Lys 445 | Asn | His | Gln |
| Val | Pro 450 | Thr | Ile | Lys | Val | His 455 | Thr | Ile | Ser | Leu | Ser 460 | Glu | Asn | Gly | Glu |
| Glu 465 | Val | | | | | | | | | | | | | | |

USE OF α-1C SPECIFIC COMPOUNDS TO TREAT BENIGN PROSTATIC HYPERPLASIA

This application is a continuation-in-part of U.S. Ser. No. 07/975,867, filed Nov. 13, 1992, now U.S. Pat. No. 5,403, 847, and a C-I-P of International Application No. PCT/US93/10950, filed 12 Nov. 1993, the contents of which are hereby incorporated by reference.

BACKGROUND OF THE INVENTION

Benign Prostatic Hyperplasia (BPH), also called Benign Prostatic Hypertrophy, is a progressive condition which is characterized by a nodular enlargement of prostatic tissue resulting in obstruction of the urethra. This results in increased frequency of urination, nocturia, a poor urine stream and hesitancy or delay in starting the urine flow. Chronic consequences of BPH can include hypertrophy of bladder smooth muscle, a decompensated bladder and an increased incidence of urinary tract infection. The specific biochemical, histological and pharmacological properties of the prostate adenoma leading to the bladder outlet obstruction are not yet known. However, the development of BPH is considered to be an inescapable phenomenon for the aging male population. BPH is observed in approximately 70% of males over the age of 70. Currently, in the United States, the method of choice for treating BPH is surgery (Lepor, H. *Urol. Clinics North Amer.,* 17, 651 (1990)). Over 400,000 prostatectomies are performed annually (data from 1986). A medicinal alternative to surgery is clearly very desirable. The limitations of surgery for treating BPH include the morbidity rate of an operative procedure in elderly men, persistence or recurrence of obstructive and irritative symptoms, as well as the significant cost of surgery.

α-Adrenergic receptors are specific neuroreceptor proteins located in the peripheral and central nervous systems on tissues throughout the body. These receptors are important switches for controlling many physiological functions and, thus, represent important targets for drug development. In fact, many α-adrenergic drugs have been developed over the past 40 years. Examples include clonidine, phenoxybenzamine and prazosin (treatment of hypertension), naphazoline (nasal decongestant), and apraclonidine (treating glaucoma). α-Adrenergic drugs can be broken down into two distinct classes: agonists (clonidine and naphazoline are agonists), which mimic the receptor activation properties of the endogenous neurotransmitter norepinephrine, and antagonists (phenoxybenzamine and prazosin are antagonists), which act to block the effects of norepinephrine. Many of these drugs are effective but also produce unwanted side effects (for example, clonidine produces dry mouth and sedation in addition to its antihypertensive effects).

During the past 15 years a more precise understanding of α-adrenergic receptors and their drugs has evolved through increased scientific scrutiny. Prior to 1977, only one α-adrenergic receptor was known to exist. Between 1977 and 1988, it was accepted by the scientific community that at least two α-adrenergic receptors—$\alpha_1$ and $\alpha_2$—existed in the central and peripheral nervous systems. Since 1988, new techniques in molecular biology have led to the identification of at least six α-adrenergic receptors which exist throughout the central and peripheral nervous systems: $\alpha_{1A}$, $\alpha_{1B}$, $\alpha_{1C}$, $\alpha_{2A}$, $\alpha_{2B}$ and $\alpha_{2C}$ (Bylund, D. B., FASEB J., 6, 832 (1992)). It is not known precisely which physiological responses in the body are controlled by each of these receptors. In addition, many α-adrenergic drugs that were developed before 1992 are not selective for any particular α-adrenergic receptor. Many of these drugs produce untoward side effects which may be attributed to their poor α-adrenergic receptor selectivity.

Since the mid 1970's, nonselective α-antagonists have been prescribed to treat BPH. In 1976, M. Caine, et al. (Brit. J. Urol., 48, 255 (1976)), reported that the nonselective α-antagonist phenoxybenzamine was useful in relieving the symptoms of BPH. This drug may produce its effects by interacting with α-receptors located on the prostate. However, this drug also produces significant side effects which severely limit its use in treating patients on a chronic basis. More recently, the α-adrenergic antagonists prazosin and terazosin have also been found to be useful for treating BPH. However, these drugs also produce untoward side effects. The most recently approved drug Proscar™ (Merck) prescribed for BPH is non an α-adrenergic antagonist, but rather acts by blocking 5-α-reductase. While Proscar is able to relieve symptoms, it is effective in only 30% of all patients, and requires a period of up to 6 months to show results.

From binding studies using cloned rat $\alpha_{1A}$, hamster $\alpha_{1B}$, and bovine $\alpha_{1C}$ receptors, and functional studies of antagonism in vitro using human prostrate, I. Marshall, et al., concluded that the receptor mediating contraction of the human prostate is of the $\alpha_{1C}$ subtype (Marshall, I., et al., Brit. Pharmacol. Soc., (1992)).

Furthermore, using cloned human receptors the binding characteristics of the known BPH drugs to various receptor subtypes have been determined, as described more fully hereinafter. Based upon such binding information and additional data, it has been observed that the side effects which occur with the drugs prazosin and terazosin may be-due to their poor selectivity for specific α-adrenergic receptors. In contrast, indoramin is a drug which is slightly selective for the human $\alpha_{1C}$ receptor relative to the other human α-adrenergic receptors, but it also interacts at human histamine H1 receptors. This compound produces untoward side effects which may be attributed to its activity at such $H_1$ receptors.

It would be desirable to provide methods and compounds which allow the treatment of BPH but which avoid the production of side effects observed for all currently used medications.

From the binding information described hereinafter, it has unexpectedly been discovered that compounds which are specific for an $\alpha_{1C}$ adrenergic receptor with a binding affinity greater than ten-fold higher than the binding affinity with which the compounds bind to an $\alpha_{1A}$ adrenergic receptor, a human $\alpha_{1B}$ adrenergic receptor, and a human histamine $H_1$ receptor, and (b) bind to an $\alpha_2$ adrenergic receptor with a binding affinity which is greater than ten-fold lower than the binding affinity with which the compounds bind to such $\alpha_{1C}$ adrenergic receptor are effective for the treatment of BPH.

Furthermore, we have characterized several antagonists selective for the $\alpha_{1C}$ adrenergic receptor using a rat orthostatic hypotension model to ascertain the vascular effects of drugs which may be indicative of their ability to produce dizziness in patients, and observed that while nonselective alpha 1 antagonists produce significant effects on orthostatic hypotension, selective alpha 1c antagonists do not produce significant effects.

SUMMARY OF THE INVENTION

The subject invention provides a method of treating benign prostatic hyperplasia in a subject which comprises administering to the subject a therapeutically effective amount of a compound which: (a) binds to a human $\alpha_{1C}$ adrenergic receptor with a binding affinity greater than ten-fold higher than the binding affinity with which the compound binds to a human $\alpha_{1A}$ adrenergic receptor, a human $\alpha_{1B}$ adrenergic receptor, and a human histamine $H_1$ receptor; and (b) binds to a human $\alpha_2$ adrenergic receptor with a binding affinity which is greater than ten-fold lower than the binding affinity with which the compound binds to such $\alpha_{1C}$ adrenergic receptor.

The subject invention also provides a method of inhibiting contraction of prostate tissue which comprises contacting the prostate tissue with an effective contraction-inhibiting amount of a compound which: (a) binds to a human $\alpha_{1C}$ adrenergic receptor with a binding affinity greater than ten-fold higher than the binding affinity with which the compound binds to a human $\alpha_{1A}$ adrenergic receptor, a human $\alpha_{1B}$ adrenergic receptor, and a human histamine $H_1$ receptor; and (b) binds to a human $\alpha_2$ adrenergic receptor with a binding affinity which is greater than ten-fold lower than the binding affinity with which the compound binds to such $\alpha_{1C}$ adrenergic receptor.

This Figure illustrates compounds which are potent antagonists of the cloned human $\alpha_{1C}$ receptor.

FIGS. 2A–2C

Figure 1:
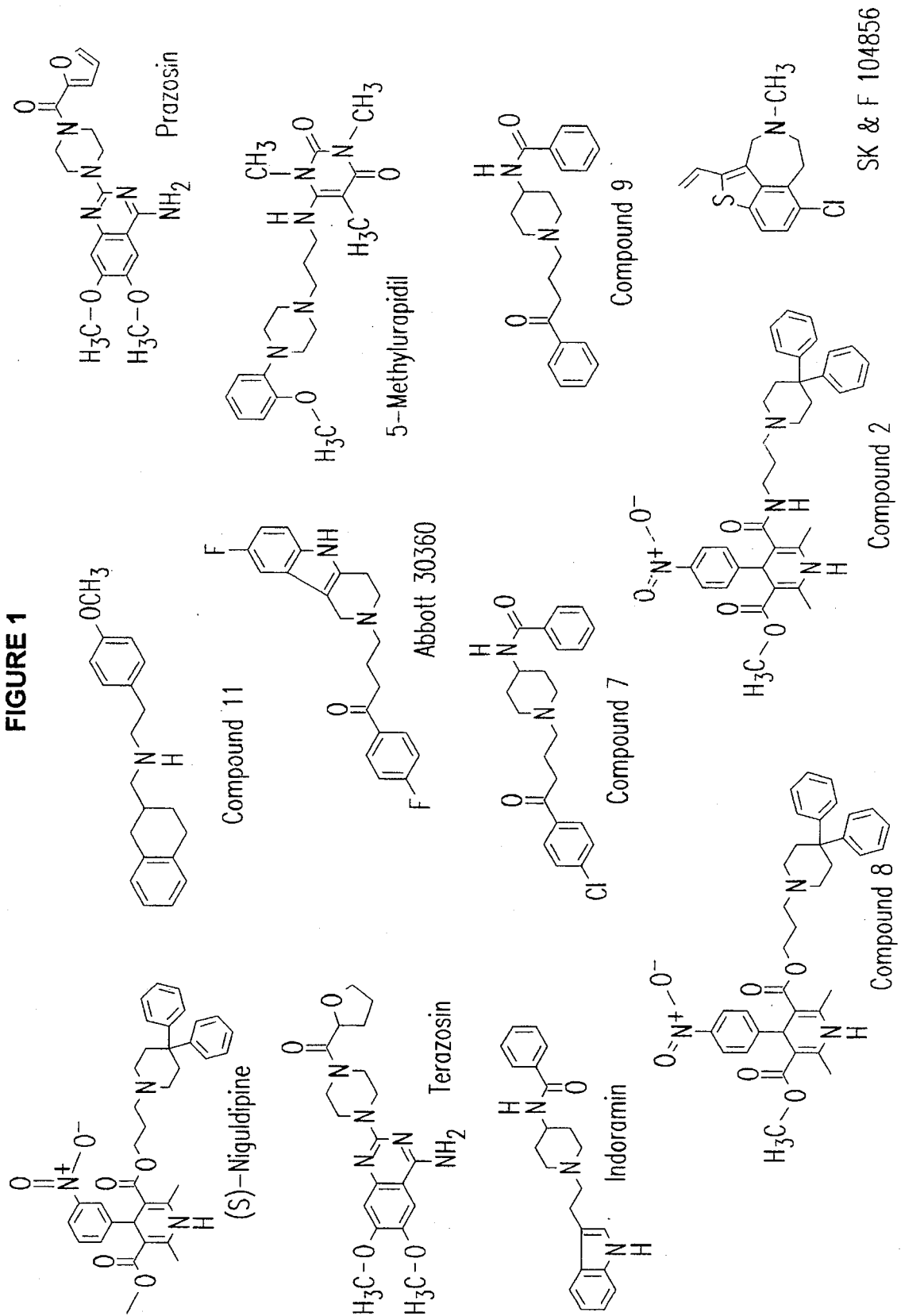
FIG. 1
Figure 2A:
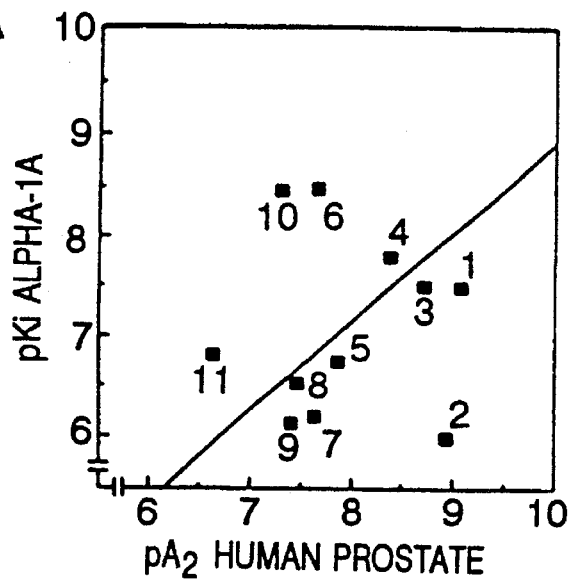

FIG. 2A illustrates the correlation of inhibition constants ($pK_i$) for a series of $\alpha_1$ antagonists at the cloned human $\alpha_{1A}$ receptors with efficiency of blocking contraction of human prostate tissue ($pA_2$).

Figure 2B:
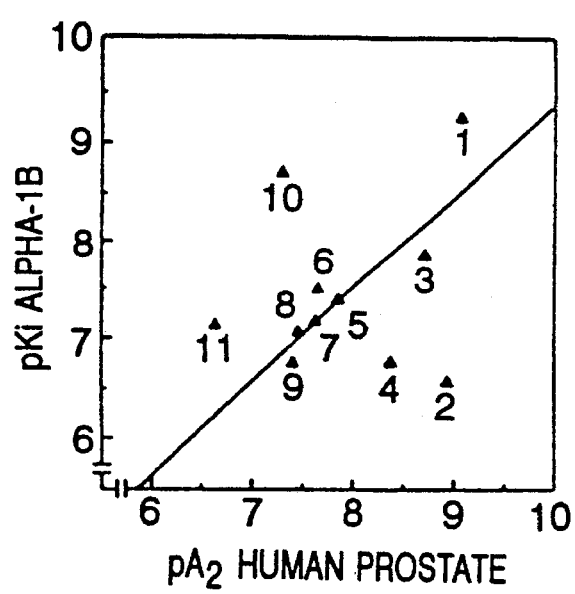

FIG. 2B illustrates the correlation of inhibition constants ($pK_i$) for a series of $a_1$ antagonists at the cloned human $\alpha_{1B}$ receptors with efficiency of blocking contraction of human prostate tissue ($pA_2$).

Figure 2C:
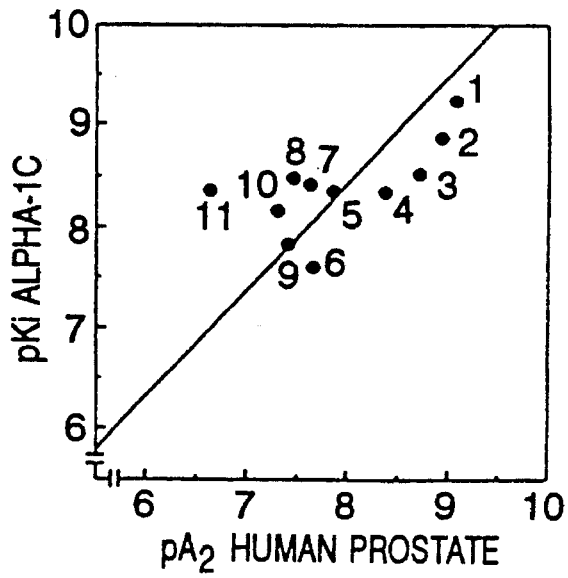

FIG. 2C illustrates the correlation of inhibition constants ($pK_i$) for a series of $\alpha_1$ antagonists at the cloned human $\alpha_{1C}$ receptors with efficiency of blocking contraction of human prostate tissue ($pA_2$).

DETAILED DESCRIPTION OF THE INVENTION

The present invention provides a method of treating benign prostatic hyperplasia in a subject which comprises administering to the subject a therapeutically effective amount of a compound which (a) binds to a human $\alpha_{1C}$ adrenergic receptor with a binding affinity greater than ten-fold higher than the binding affinity with which the compound binds to a human $\alpha_{1A}$ adrenergic receptor, a human $\alpha_{1B}$ adrenergic receptor, and a human histamine $H_1$ receptor, and (b) binds to a human $\alpha_2$ adrenergic receptor with a binding affinity which is greater than ten-fold lower than the binding affinity with which the compound binds to such $\alpha_{1C}$ adrenergic receptor.

Ten-fold selectivity differences are a minimum, but one skilled in the art will appreciate that compounds can be found that collectively have almost infinitely variable selectivity profiles. Compounds collectively having all possible combinations of selectivities are intended within the scope of this invention, provided that each of these compounds has at least a ten-fold greater selectivity for the $\alpha_{1C}$ receptor over the $\alpha_{1A}$, $\alpha_{1B}$, $\alpha_2$ and $H_2$ receptors. For example, compounds useful in the methods of this invention can have at least a 10, 20, 30, 40, 50, 75, 100, 200, 300 or greater fold selectivity for binding to the $\alpha_{1C}$ receptor over binding to the $\alpha_{1A}$, $\alpha_{1B}$, $\alpha_2$ and $H_1$ receptors. The compounds useful in the methods of this invention can also have selectivity for the $\alpha_{1C}$ receptor over the $\alpha_{1A}$, $\alpha_{1B}$, $\alpha_2$ and $H_2$ receptors, such selectivity having a number-fold between these exemplary integers. Furthermore, these compounds can additionally have selectivity within the ranges described above for binding to the $\alpha_{1C}$ receptor over binding to (1) a calcium channel; and/or (2) a $D_2$ or $H_2$ receptor; and/or (3) any serotonin receptor; and/or (4) a dopamine $D_3$, $D_4$ or $D_5$ receptor.

In the preferred embodiment, the compound (a) binds to a human $\alpha_{1C}$ adrenergic receptor with a binding affinity greater than 20-, 50-, 100- or 300-fold higher than the binding affinity with which the compound binds to a human $\alpha_{1A}$ adrenergic receptor, a human $\alpha_{1B}$ adrenergic receptor, and a human histamine $H_1$ receptor, and (b) binds to a human $\alpha_2$ adrenergic receptor with a binding affinity which is greater than 20-, 50-, 100- or 300-fold lower than the binding affinity with which the compound binds to such $\alpha_{1C}$ adrenergic receptor.

Desirably, the compound used to practice the method of the invention additionally binds to a calcium channel with a binding affinity which is greater than ten-fold lower than the binding affinity with which the compound binds to the $\alpha_{1C}$ adrenergic receptor.

In the preferred embodiment, the compound binds to a calcium channel with a binding affinity which is greater than 20-, 50-, 100- or 300-fold lower than the binding affinity with which the compound binds to the $\alpha_{1C}$ adrenergic receptor.

Alternatively or incrementally, the compound used to practice the method of the invention additionally binds to a dopamine $D_2$ receptor or human $H_2$ receptor with a binding affinity which is greater than ten-fold lower than the binding affinity with which the compound binds to the $\alpha_{1C}$ adrenergic receptor.

In the preferred embodiment, the compound binds to a human dopamine $D_2$ or human $H_2$ receptor with a binding affinity which is greater than 20-, 50-, 100- or 300-fold lower than the binding affinity with which the compound binds to the $\alpha_{1C}$ adrenergic receptor.

Alternatively or incrementally, the compound used to practice the method of the invention additionally binds to any serotonin receptor with a binding affinity which is greater than ten-fold lower than the binding affinity with which the compound binds to the $\alpha_{1C}$ adrenergic receptor.

In the preferred embodiment, the compound binds to any serotonin receptor with a binding affinity which is greater than 20-, 50-, 100- or 300-fold lower than the binding affinity with which the compound binds to the $\alpha_{1C}$ adrenergic receptor.

Alternatively or incrementally, the compound used to practice the method of the invention also binds to a human dopamine $D_3$, $D_4$ or $D_5$ receptor with a binding affinity which is greater than ten-fold lower than the binding affinity with which the compound binds to the $\alpha_{1C}$ adrenergic receptor.

In the preferred embodiment, the compound binds to a dopamine $D_3$, $D_4$, or $D_5$ receptor with a binding affinity which is greater than 20-, 50-, 100- or 300-fold lower than the binding affinity with which the compound binds to the $\alpha_{1C}$ adrenergic receptor.

Alternatively or incrementally, the compound used to practice the method of the invention also does not cause orthostatic fall in blood pressure at a dosage effective to alleviate benign prostatic hyperplasia.

In one embodiment, the compound used to practice the method of the invention also does not cause orthostatic fall in blood pressure in rats at a dosage 10 ug/kg.

A number of compounds have been identified or synthesized which are useful in the practice of the invention. For example, the compound has the structure:

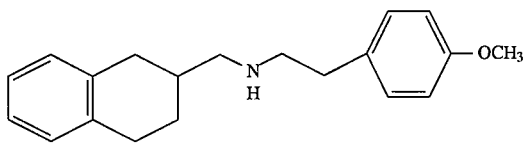

In another example, the compound has the structure:

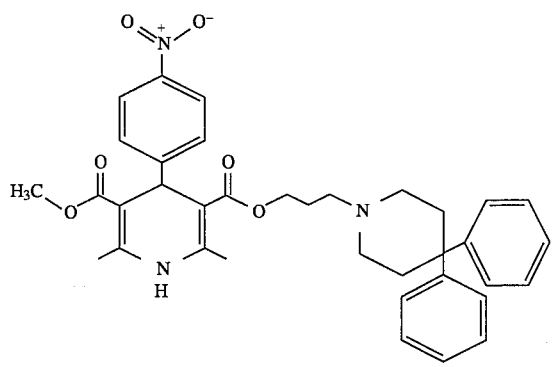

In still another example, the compound has the structure:

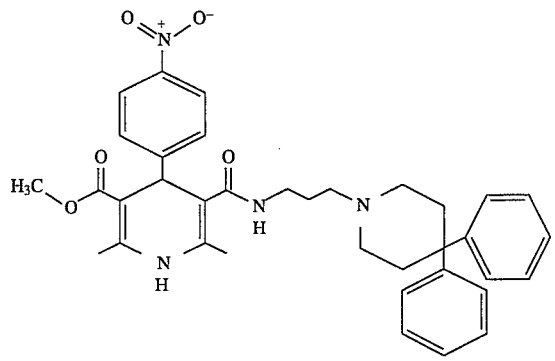

In an additional example, the compound has the structure:

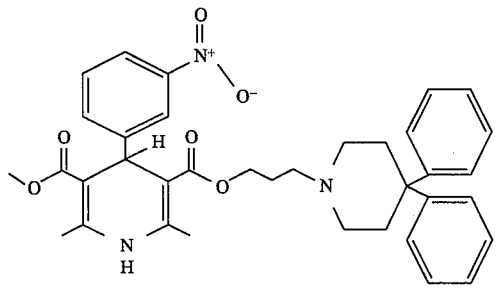

Included within the scope of the method of treating BPH in accordance with the invention are the use of both R and S enantiomers of the compounds described which possess stereogenic centers, as well as the use of pharmaceutically acceptable salts and complexes thereof.

The invention also provides a method of inhibiting contraction of prostate tissue which comprises contacting the prostate tissue with an effective contraction-inhibiting amount of a compound which (a) binds to a human $\alpha_{1C}$ adrenergic receptor with a binding affinity greater than ten-fold higher than the binding affinity with which the compound binds to a human $\alpha_{1A}$ adrenergic receptor, a human $\alpha_{1B}$ adrenergic receptor, and a human histamine $H_1$ receptor, and (b) binds to a human $\alpha_2$ adrenergic receptor with a binding affinity which is greater than ten-fold lower than the binding affinity with which the compound binds to such $\alpha_{1C}$ adrenergic receptor.

In the preferred embodiment, the compound (a) binds to a human $\alpha_{1C}$ adrenergic receptor with a binding affinity greater than 20-, 50-, 100- or 300-fold higher than the binding affinity with which the compound binds to a human $\alpha_{1A}$ adrenergic receptor, a human $\alpha_{1B}$ adrenergic receptor, and a human histamine $H_1$ receptor, and (b) binds to a human $\alpha_2$ adrenergic receptor with a binding affinity which is greater than 20-, 50-, 100- or 300-fold lower than the binding affinity with which the compound binds to such $\alpha_{1C}$ adrenergic receptor.

The activity of compounds at the different human receptors was determined in vitro using cultured cell lines that selectively express the receptor of interest. These cell lines were prepared by transfecting the cloned cDNA or cloned genomic DNA or constructs containing both genomic DNA and cDNA encoding the human $\alpha$-adrenergic, serotonin, histamine, and dopamine receptors as further described in detail in Example 9 hereinbelow.

In connection with this invention, a number of cloned human receptors discussed herein, either as plasmids or as stably transfected cell lines, have been made pursuant to, and in satisfaction of, the Budapest Treaty on the International Recognition of the Deposit of Microorganisms for the Purpose of Patent Procedure, and are made with the American Type Culture Collection, 12301 Parklawn Drive, Rockville, Md. 20852. Specifically, these deposits have been accorded ATCC Accession Numbers as follows:

| Designation | ATCC Accession No. | Date |
| --- | --- | --- |
| L-$\alpha_{1A}$ | CRL 11138 | September 25, 1992 |
| L-$\alpha_{1B}$ | CRL 11139 | September 25, 1992 |
| L-$\alpha_{1C}$ | CRL 11140 | September 25, 1992 |
| L-$\alpha_{2A}$ | CRL 11180 | November 6, 1992 |
| L-NGC-$\alpha_{2B}$ | CRL 10275 | October 25, 1989 |
| L-$\alpha_{2C}$ | CRL 11181 | November 6, 1992 |
| pcEXV-$H_1$ | 75346 | November 6, 1992 |
| pcEXV-$H_2$ | 75345 | November 6, 1992 |
| pcEXV-$D_2$ | 75344 | November 6, 1992 |

The data shown in the accompanying Tables indicate that the $\alpha_{1C}$-specific receptor antagonists which satisfy the criteria as defined herein have significant efficacy in the inhibition of contraction of human prostate tissue. This in vitro property is recognized in the art as correlating with efficacy in treating benign prostatic hyperplasia in vivo.

The present invention therefore provides a method of treating benign prostatic hyperplasia, which comprises administering a quantity of any of the $\alpha_{1C}$ receptor antagonists defined as herein in a quantity effective against BPH. The drug may be administered to a patient afflicted with benign prostatic hyperplasia by any conventional route of administration, including, but not limited to, intravenous, intramuscular, oral, subcutaneous, intratumoral, intradermal, and parenteral. The quantity effective against BPH is between 0.001 mg and 10.0 mg per kg of subject body weight.

The method of treating BPH disclosed in the present invention may also be carried out using a pharmaceutical composition comprising any of the $\alpha_{1C}$ receptor antagonists as defined herein and a pharmaceutically acceptable carrier. The composition may contain between 0.05 mg and 500 mg of an $\alpha_{1C}$ receptor antagonist, and may be constituted into any form suitable for the mode of administration selected. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

The drug may otherwise be prepared as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes, and coatings.

Optimal dosages to be administered may be readily determined by those skilled in the art, and will vary with the particular $\alpha_{1C}$ receptor antagonist in use, the strength of the preparation, the mode of administration, and the advancement of the disease condition. Additional factors depending on the particular patient being treated will result in a need to adjust dosages, including patient age, weight, diet, and time of administration.

The following Experimental Details are set forth to aid in an understanding of the invention, and are not intended, and should not be construed, to limit in any way the invention set forth in the claims which follow thereafter.

EXPERIMENTAL DETAILS

Prazosin, 5-methylurapidil, and S-niguldipine were obtained from Research Biochemicals, Inc. A30360 (4-fluoro-4-(8-fluoro-1,3,4,5-tetrahydro-2H-pyrido[4,3-b]indol-2-yl)butyrophenone hydrochloride) was obtained from Aldrich Chemical Co. Other compounds were prepared according to the examples which follow.

EXAMPLE 1

Synthesis of Terazosin Hydrochloride

N-(2-Furoyl)piperazine

This compound and its preparation has been described in Great Britain Patents 1,390,014 and 1,390,015. Piperazine hexahydrate (194 g, 1 mole) was dissolved in 250 ml $H_2O$. The solution was acidified to pH 4.5 with 6N HCl. Furoyl chloride (130.5 g, 1 mole, Aldrich) was added along with 10% NaOH solution at such a rate that the pH was maintained at 4.5. After 1 hour, the solution was made basic (pH=8.5) with NaOH solution. The reaction mixture was continuously extracted with chloroform for 36 hours. The $CHCl_3$ extract was dried over $MgSO_4$, and filtered. Distillation gave 108.2 g product (60%), b.p. 132°–138° C./0.6 mm Hg, m.p. 69°–70° C.

N-(Tetrahydro-2-furoyl)piperazine

The furoylpiperazine of Example 1 was converted to the hydrobromide salt (m.p. 173°–175° C.). This salt (39.0 g) in 250 ml methyl alcohol and 9.0 g Raney nickel was hydrogenated at 3 atm. After uptake of $H_2$ ceased, the catalyst was filtered, the solvent concentrated, and the residue crystallized from isopropyl alcohol to give 35.2 g. tetrahydrofuroylpiperazine HBr, m.p. 152°–156° C. This was suspended in 20 ml $H_2O$. Then 10.5 g 50%, NaOH solution was added slowly followed by 2.0 g solid $Na_2CO_3$.

This was extracted with 4×100 ml portions of warm $CHCl_3$. The $CHCl_3$ extractions were distilled to give 22.5 g tetrahydrofurolylpiperazine, b.p. 120°–125° C./0.2 mm Hg.

2[4-(Tetrahydro-2-furoyl)piperazinyl]-4-amino-6,7-dimethoxyquinazoline hydrochloride To 7.00 g 2-chloro-4-amino-6,7-dimethoxyquinazoline (Lancaster Synthesis) in 50 ml methoxyethanol was added 10.8 g, tetrahydrofurolylpiperazine, and the mixture refluxed 3 hours. The clear solution was concentrated and an aqueous solution of potassium bicarbonate was added. The resultant solid that formed was filtered and washed with water. It was then added to methanol and the resulting suspension was acidified with a solution of hydrogen chloride in isopropyl alcohol. The resulting solution was concentrated and the residue crystallized from isopropyl alcohol giving 8.12 g. of product, m.p. 278°–279° C.

EXAMPLE 2

Preparation of Indoramin

4-Benzamido-1-[2-(3-indolyl)ethylpyridinium Bromide

A solution of 4-benzamidopyridine (1.98 g) and 3-(2-bromoethyl)indole (2.24 g) in EtOH (15 ml) was refluxed for 2 hours, and the crystallized product (3.13 g, mp 264°–266° C.) was collected by filtration from the hot reaction mixture. Recrystallization gave the hydrate.

3-[2-4-Benzamidopiperid-1-yl)ethyl]indole (Indoramin)

4-Benzamido-1-[2-(3-indolyl)ethyl]pyridinium bromide (3.0 g) in 91% EtOH (300 ml) containing $Et_3N$ (0.8 g) was hydrogenated in the presence of freshly prepared W-7 Raney Ni catalyst (ca. 3 g) at 28.12 kg/$cm^2$ and 50° for 4 hours. After filtering off the catalyst, the filtrate was evaporated and the residue was shaken with $CHCl_3$ and 2N NaOH. The resulting insoluble material (1.61 g, mp 203°–206° C.) was collected and dried. Recrystallization from EtOH gave the product (1.34 g), as colorless needles.

EXAMPLE 3

Preparation of 1-(3-benzoylpropyl)-4-benzamidopiperidine

A mixture of 4-chlorobutyrophenone (447 mg, 2.45 mmol), 4-benzamidopiperidine (500 mg, 2.45 mmol) and $K_2CO_3$ (338 mg, 2.45 mmol) was heated up in boiling water bath for 1 hour. The reaction mixture was portioned between water and $CHCl_3$. The organic layer was separated and dried over $Na_2SO_4$. After filtration and removal of solvent, the residue was purified by chromatography ($SiO_2$, MeOH:$CHCl_3$, 5:95). Recrystallization from AcOEt/hexane gave a white powder (78 mg, 8.2%). mp 143°–144° C.; $^1$H NMR ($CD_3OD$, 400 MHz) δ 1.65 (dq, $J_1$=3.16 Hz, $J_2$=11.9 Hz, 2H), 1.90–2.00 (m, 4H), 2.18 (t, J=11.9 Hz, 2H), 2.48 (m, 2H), 3.00–3.10 (m, 4H), 3.88 (m, 1H), 7.40–8.00 (m, 10H); Mass spectrum (M+1)$^+$ at m/z 351.

EXAMPLE 4

Preparation of 1-[3-(4-chlorobenzoyl)propyl]-4-amidopiperidine

A mixture of 3-(4-chlorobenzol)propyl bromide (640 mg, 2.45 mmol), 4-benzamidopiperidine (500 mg, 2.45 mmol) and $K_2CO_3$ (1.01 g, 7.34 mmol) in 50 ml of acetone was heated up to refluxing condition for 48 hours. The solid was removed by filtration. Concentration of filtrate in vacuo gave a yellowish solid, which was purified by chromatography (SiO$_2$, MeOH:CHCl$_3$, 5:95). 320 mg (33.9%) of white powder was obtained $^1$H NMR (CDCl$_3$, 300 mHz) δ 1.46 (dq, J$_1$=1.0 Hz, J$_2$=8.4 Hz, 2H), 1.90–2.10 (m, 4H), 2.16 (m, 2H), 2.43 (t, J=6.9 Hz, 2H), 2.80–2.90 (m, 2H), 2.97 (t, J=6.9 Hz, 2H), 3.97 (m, 1H), 5.92 (d, J=7.8 Hz, 1H, N-H), 7.40–8.00 (m, 9H); Product was converted to HCl salt and recrystallized with MeOH/Et$_2$O, mp 243°–244° C.; Calcd for C$_{22}$H$_{25}$ClN$_2$O$_2$·HCl·H$_2$O: C 60.15, H 6.37, N 6.37; Found: C 60.18, H 6.34, N6.29.

EXAMPLE 5

Preparation of SKF-104856

1-[(4-Chlorophenyl)thio}-2-propanone

Chloroacetone (32.3 g, 0.347 mol) was added to a mixture of 4-chlorothiophenol (50 g, 0.347 mmol) and sodium hydroxide (14 g, 0.347 mol) in water (400 ml) and the mixture was stirred at 25° C. for 1 hour. The mixture was extracted with ethyl ether and the organic phase was washed with water, dried with magnesium sulfate and concentrated to give 69 g (99%) of 1-[(4-chlorophenyl)thio]-2-propanone.
5-Chloro-3-methylbenzo(b)thiophene 1-[(4-Chlorophenyl)thio}-2-propanone (50 g, 0.25 mol) was added to polyphosphoric acid (300 g) and the mixture was stirred as the temperature was gradually raised to 120° C. as an exotherm started. The mixture was stirred at 130° C. for 1 hour, diluted with water, extracted with ethyl ether and the organic phase was dried and concentrated. The residue was stirred in methanol (200 ml), filtered and the filtrate concentrated to give 17.5 g (40%) of 5-chloro-3-methylbenzo(b)thiophene: bp 120° C. (0.6 mm Hg).
Ethyl 5-chloro-3-methylbenzo(b)thiophene-2-carboxylate n-Butyllithium in hexane (2.6M, 2.3 ml) was added to a solution of 5-chloro-3-methylbenzo(b)thiophene (1,0 g, 6 mmol) in ethyl ether (20 ml) stirred at 0° C. under argon. The mixture was stirred for 30 minutes and transferred slowly under argon pressure to a stirred solution of ethyl chloroformate (0.63 g, 6 mmol) in ethyl ether (20 ml). The mixture was stirred at 0° C. for 30 minutes and at 25° C. for 1.5 hours. The mixture was treated with water and the organic phase was dried, concentrated and triturated with hexane to give 1.0 g (67%) of ethyl 5-chloro-3-methylbenzo(b) thiophene-2-carboxylate: mp 92.5°–94° C.
Ethyl 3-bromomethyl-5-chlorobenzo(b)thiophene-2-carboxylate A mixture of ethyl 5-chloro-3-methylbenzo(b)thiophene-2-carboxylate (9.0 g, 0.035 mol), N-bromosuccinimide (6.53 g, 0.037 mol) and benzoyl peroxide (130 mg) in carbon tetrachloride (150 ml) was refluxed and illuminated with sunlamp for 2 hours. The resulting suspension was cooled, filtered and the filter cake was triturated with methanol to give 9.9 g, (85%) of the methanol-insoluble ethyl 3-bromomethyl-5-chlorobenzo(b)thiophene-2-carboxylate: mp 148°–150° C.
Ethyl 5-Chloro-3-[N-(2,2-dimethoxyethyl)-N-methyl(aminomethyl)]benzol(b)thiophene-2-carboxylate A mixture of ethyl 3-bromomethyl-5-chlorobenzo(b) thiophene-2-carboxylate (11 g, 0.033 mol), methylaminoacetaldehyde dimethyl acetal (4.76 g, 0.04 mol) and potassium carbonate (11.4 g, 0.8 mol) in dry acetone (200 ml) was stirred for 48 hours, filtered and the filtrate concentrated to give 11.8 g, (96%) of ethyl 5-chloro-3-(N-2,2-dimethoxyethyl)-N-methyl(aminomethyl)benzol(b)thiophene-2-carboxylate.
Ethyl 7-chloro-3,4-dihydro-4-methylthieno[4,3,2-ef]-[3] benzazepine-2-carboxylate Ethyl 5-chloro-3-[N-(2,2-dimethoxyethyl)-N-methyl (aminomethyl)]benzo[b]thiophene-2-carboxylate (3.0 g, 8.1 mmol) was added in portions to trifluoromethanesulfonic acid (10 ml) stirred at 0° C. under argon. The mixture was stirred at 25° C. for 45 minutes and diluted with water. The mixture was basified with aqueous sodium hydroxide and extracted with ethyl ether to give ethyl 7-chloro-3,4-dihydro-4-methylthieno-[4,3,2-ef][3]benzazepine-2-carboxylate.
Ethyl 7-chloro-3,4,5,6-tetrahydro-4-methylthieno[4,3,2-ef][3]benzazepine-2-carboxylate Diborane in tetrahydrofuaran (1M, 40 ml) was added to a solution of ethyl 7-chloro-3,4-dihydro-4-methylthieno -[4,3,2-ef][3]benzazepine-2-carboxylate (2.8 g) in tetrahydrofuran (30 ml) stirred at 0° C. The mixture was refluxed for 3 hours and stirred at 25° C. for 18 hours, cooled, treated with methanol (50 ml), refluxed for 18 hours and concentrated. The residue was triturated with ethyl ether-hexane (3:1) to give 1.6 g (84%) of ethyl 7-chloro-3,4,5,6-tetrahydro-4-methylthieno[4,3,2-ef][3]-benzazepine-2-carboxylate: mp 138°–140° C. The free base was treated with hydrogen chloride to give ethyl 7-chloro-3,4,5,6-tetrahydro-4-methylthieno[4,3,2-ef][3]benzazepine-2-carboxylate hydrochloride: mp 240° C.
7-Chloro-3,4,5,6-tetrahydro-4-methylthieno[4,3,2-ef][3] benzazepine-2-methanol A solution of ethyl 7-chloro-3,4,5,6-tetrahydro-4-methylthieno [4.3.2-ef][3]benzazepine-2-carboxylate (4.0 g, 12.9 mmol), in ethyl ether (48 ml) was treated with lithium aluminum hydride (0.53 g, 14 mmol). The mixture was stirred for 1.5 hours, cooled and treated carefully with water (2.0 ml), 10% sodium hydroxide (1.0 ml) and water (2.0 ml). The resulting mixture was filtered and the solvent evaporated to give 1.9 g (57%) of 7-chloro -3,4,5,6-tetrahydro-4-methylthieno[4,3,2-ef][3]benzazepine -2-methanol: mp 184°–185° C.
7-Chloro-3,4,5,6-tetrahydro-4-methylthieno-4,3,2-ef][3] benzazepine-2-carboxaldehyde A solution of 7-chloro-3,4,5,6-tetrahydro-4-methylthieno [4,3,2-ef][3]benzazepine-2-methanol (1.6 g, 6 mmol) in dichloromethane (150 ml) was stirred under argon with activated manganese dioxide (8.3 g) for 2 hours. The mixture was filtered through Celite™ and the filtrate was dried with magnesium sulfate and concentrated to give a 63% yield of 7-chloro-3,4,5,6-tetrahydro -4-methylthieno4,3,2-ef [[3]benzazepine-2-carboxaldehyde.
7-Chloro-2-ethenyl-3,4,5,6-tetrahdyro-4-methylthieno[4,3, 2-ef][3]benzazepine (SKF-104856)

Sodium hydride (60% dispersion in mineral oil. 3.8 mmol) was added to a stirred solution of methyltriphenylphosphonium bromide (1.35 g, 3.8 mmol) in dry tetrahydrofuran (30 ml) and stirred for 15 minutes. The mixture was treated with a solution of 7-chloro-3,4,5,6-tetrahydro-4-methylthieno[4,3,2-ef][3]-benzazepine-2-carboxaldehyde, prepared as in Example 3, (0.5 g, 1.9 mmol) in dimethyl-formamide (4 ml), stirred at 25° C. for 16 hours, quenched with ice and extracted with ethyl acetate. The organic phase was washed, dried and concentrated and the residue was chromatographed on silica gel eluted with a gradient of methylene chloride to methanol-methylene chloride (3.5:96.5). The product was treated with hydrogen chloride to give 0.2 g (35%) of 7-chloro-2-ethenyl-3,4,5,6-tetrahydro-4-methylthieno[4,3,2-ef][3]benzazepine hydrochloride: mp 234°–236° C.

EXAMPLE 6

2-Hydroxymethyl-1,2,3,4-tetrahydronaphthalene

A solution of 1,2,3,4-tetrahydro-2-naphthoic acid (2.50 g, 14.2 mmol) in 100 ml THF was treated with LiAlH$_4$ (681 mg, 17.04 mmol) and the reaction mixture was heated at reflux for 5 hours. The suspension was cooled to 0° C. and quenched by addition of solid Na$_2$SO$_4$■10H$_2$O. The mixture was stirred at room temperature for 4 hours. The solid was removed by filtration. Concentration of filtrate in vacuo gave a yellowish oil (2.28 g, 98.8%); $^1$H NMR (CDCl$_3$, 300 MHz) δ 1.43 (m, 1H), 2.00 (m, 2H) 2.51 (dd, J$_1$=16.5 Hz, J$_2$=10.8 Hz, 1H), 2.85 (m, 3H), 3.65 (dd, J$_1$=6.3 Hz, J$_2$=1.2 Hz, 2H), 7.09 (s, 4H).

2-Bromomethyl-1,2,3,4-tetrahydronaphthalene

A solution of 2-hydroxymethyl-1,2,3,4-tetrahydronaphthalene (2.28 g, 14.0 mmol) in 100 ml of CH$_2$Cl$_2$ was treated with PBr$_3$ (1.28 g, 4.73 mmol) at 0° C. The mixture was stirred at room temperature for 72 hours then poured onto 100 g of ice. The organic layer was isolated, washed with 10% K$_2$CO$_4$ aqueous solution, H$_2$O, sat'd brine, and then dried over Na$_2$SO$_4$. After filtration and removal of solvent, the residue was purified by chromatography (SiO$_2$, EtOAc:hexane, 1:10) to give a colorless oil (1.33 g, 41.6%); $^1$H NMR (CDCl$_3$, 300 MHz) δ 1.55 (m, 1H), 2.11 (m, 1H), 2.11 (m, 2H), 2.58 (dd, J$_1$=16.2 Hz, J$_2$=10.2 Hz, 1H), 2.80–3.10 (m, 3H), 3.45 (d, J=6.3 Hz, 2H), 7.10 (m, 4H).

2-[(4-Methoxyphenethyl)aminomethyl]-1,2,3,4-tetrahydronaphthalene (Compound 11)

A solution of 2-bromomethyl-1,2,3,4-tetrahydronaphthalene (1.33 g, 5.91 mmol) and 4-methoxyphenethylamine (1.79 g, 11.8 mmol) in 50 ml of EtOH was refluxed for 48 hours. After removal of EtOH in vacuo, the residue was dissolved in 100 ml of CHCl$_3$, washed with 10% K$_2$CO$_3$, H$_2$O, sat'd brine, and then dried over Na$_2$SO$_4$. Filtration followed by evaporation of solvent gave a yellow oil, which was purified by chromatography (SiO$_2$, MeOH:CHCl$_3$, 5:95) to a give a yellowish oil (1.03 g, 58.9%). The product was converted to HCl salt, crystallization with MeOH/Et$_2$O gave a white powder. mp 274°–275° C.; Calcd for C$_{20}$H$_{25}$NO.HCl: C 72.37, H 7.91, N 4.22; Found C 72.40, H 7.76, N 4.13.

EXAMPLE 7

4,4-Diphenylpiperidine hydrochloride

A mixture of 4-piperidone monohydrate hydrochloride (15.0 g, 97.6 mmol, 1.00 equiv, Aldrich) and AlCl$_3$ (130 g, 976 mmol, 10.0 equiv) in anhydrous benzene (600 mL) was stirred at reflux for 4 hours. Ice (300 g) and water (50 mL) were added, the mixture was filtered, and the solid was washed with toluene and dried to afford 19.2 g (72%) of off-white solid, which was pure by $^1$H NMR. Recrystallization from ethanol gave the analytically pure sample: m.p. 300°–301° C.; $^1$H NMR (300 MHz, CD$_3$OD) δ 2.65 (m, 4 H), 3.18 (m, 4 H), 7.18 (m, 2 H), 7.30 (m, 8 H); Anal. Calcd. for C$_{17}$H$_{19}$N·HCl: C, 74.57; H. 7.36; N, 5.12. Found: C, 74.32; H, 7.34; N, 5.02. The free base was generated by addition of the above salt to dilute aqueous sodium hydroxide and extraction with CH$_2$Cl$_2$. The organic phase was dried over MgSO$_4$ and concentrated to give a light brown solid: IR (neat) 2942.8, 1494.5, 1445.9 cm$^{-1}$; CIMS (NH$_3$) m/e 238 (M+1)$^+$.

3-(4,4-Diphenylpiperidin-1-yl)propionitrile

To a suspension of 4,4-diphenylpiperidine hydrochloride (195 mg, 0.712 mmol, 1.0 equiv) in ETOh (1.5 mL) was added triethylamine (0.25 mL, 1.83 mmol, 2.6 equiv) followed by acrylonitrile (0.13 mL, 2.01 mmol, 2.8 equiv). The resulting solution was stirred at room temperature under argon for 15 minutes and then concentrated. Water was added, and the mixture was extracted three times with EtOAc. The combined organic extracts were dried over MgSO$_4$ and concentrated to give 170 mg (87%) of tan solid, which was used for the next reaction without purification. m.p. 95°–96° C.; $^1$H NMR (300 MHz, CDCl$_3$) δ 2.37 (m, 2H), 2,46 (m, 4H), 2.52 (m, 6H), 7.12 (m, 2H), 7.23 (m, 8H); $^{13}$C NMR (75 MHz, CDCl$_3$) δ 16.65, 36.71. 45.08, 50.78, 54.13, 119.70, 126.48, 127.78, 129.11, 147.87; IR (neat) 2944.4, 2821.0, 1495.5, 1445.9 cm$^{-1}$.

1-(3-Aminopropyl)-4,4-diphenylpiperidine

To a stirred solution of 3-(4,4-diphenylpiperidine-1-yl) propionitrile (2.00 g, 6.89 mmol, 1.0 equiv) in anhydrous THF (20 mL) under argon was added a solution of BH$_3$ in THF (1.0M, 24.1 mL, 24 mmol, 3.5 equiv) at room temperature. The mixture was refluxed for 4.5 hours and then cooled to room temperature. Aqueous HCl (6N, 50 mL) was added and stirring was continued for 1 hour. The mixture was basified to pH 9 by addition of 6N aq. NaOH, extracted 3 times with CH$_2$Cl$_2$, dried over MgSO$_4$ and concentrated. The residue was purified by flash chromatography (SiO$_2$, EtOAc-MeOH, 9:1, followed by EtOAc -MeOH-isopropylamine (60:10:1), followed by EtOAc-MeOH-isopropylamine (40:10:2) to give 1.35 g (66%) of tan solid: m.p. 98°–99° C.; $^1$H NMR (300 MHz, CDCl$_3$) δ 1.64 (tt, J=7.7 Hz, 2H), 2.33 (br t, J=7.2 Hz, 2H), 2.50 (m, 8H), 2.76 (br t, J=6.5 Hz, 2H), 3.06 (br s, 2H), 7.13 (m, 2H), 7.26 (m, 8H); $^{13}$C NMR (75 MHz, CDCl$_3$) δ 29.79, 36.80, 41.41, 45.24, 51.25, 57.41, 126.30, 127.77, 128.97, 148.11; IR (neat) 3361.5 cm$^{-1}$; CIMS (NH$_3$) m/e 295 (M+1)$^+$.

Acetoacetic acid N-[3-(4,4-diphenylpiperidin-1-yl)propyl] amide

Diketene (0.44 mL, 5.68 mmol, 1.3 equiv, Aldrich) was added at room temperature to a stirred solution of 1-(3-aminopropyl) -4,4-diphenylpiperidine (1.288 g, 4.37 mmol, 1.0 equiv) in anhydrous toluene (15 mL) under argon, and stirring was continued for 48 hours. The mixture was concentrated to give 1.294 g (78%) of white solid, which was used for the next reaction without purification: $^1$H NMR (300 MHz, CDCl$_3$) δ 1.70 (tt, J=6.4, 6.4 Hz, 2H), 2.23 (s, 3H), 2.44 (br t, J=6.5 Hz), 2.49–2.67 (m, 8H), 3.32 (br t, J=5.8 Hz), 3.36 (s, 2H), 7.16 (m, 2H), 7.27 (m, 8H).

2,6-Dimethyl-4-(4-nitrophenyl)-1,4-dihydropyridine-3,5-dicarboxylic acid N-[3-(4,4-diphenylpiperidine-1-yl)propyl] amide methyl ester A solution of acetoacetic acid N-[3-(4,4-diphenylpiperidin-1-yl)propyl]amide (365 mg, 0.964 mmol, 1.0 equiv), methyl 3-aminocrotonate (138 mg, 1.20 mmol, 1.2 equiv, Aldrich), and 4-nitrobenzaldehyde (181 mg, 1.20mmol, 1.2 equiv, Aldrich) in isopropanol was refluxed under argon for 60 hours. The mixture was cooled to room temperature and concentrated, and the residue was diluted with CH$_2$Cl$_2$, washed with water, dried over MgSO$_4$, and concentrated. The residue was purified by flash chromatography (SiO$_2$, EtOAc, followed by EtOAc-MeOH, 19:1 and 9:1) to give 147.8 mg (25%) of yellow solid: $^1$H NMR (300 MHz, CDCl$_3$) δ 1.55 (m, 2H), 2.14 (s, 3H), 2.15–2.50 (m, 10H), 2.32 (s, 3H), 3.20 (m, 1H), 3.37 (m, 1H), 3.54 (s, 3H), 5.00 (s, 3H), 5.48 (br s), 6.98 (br t, J=4.9 Hz, 1H), 7.14–7.30 (m, 10H), 7.39 (dm, J=8.7 Hz, 2H), 8.05 (dm, J=8.7 Hz, 2H); $^-$C NMR (75 MHz, CDCl$_3$) δ 18.74, 20.64, 25.61, 36.77, 40.20, 42.26, 45.03, 51.16, 51.61, 58.08, 100.65, 109.71, 124.35, 126.46, 127.61, 128.84, 129.06, 135.52, 146.96, 147.10, 154.55, 168.22, 168.70; IR (neat) 1680, 1610, 1515, 1340 cm$^{-1}$; MS (FAB) m/e 609 (M+H)$^+$.

2,6-Dimethyl-4-(4-nitrophenyl)-1,4-dihydropyridine-3,5-dicarboxylic acid N-[3-(4,4-diphenylpiperidin-1-yl)propyl] amide methyl ester hydrochloride hydrate (Compound 2)

To a solution of 2,6-dimethyl-4-(4-nitrophenyl)-1,4-dihydropyridine-3,5-dicarboxylic acid N-[3-(4,4-diphenylpiperidin-1-yl)propyl]amide methyl ester (147.8 mg, 0.243 mmol, 1.0 equiv) in EtOH (2 mL) was added a solution of HCl in ether (1.0M, 0.24 mL, 0.24 mmol, 1.0 equiv). Addition of ethyl acetate (3 mL) followed by heating gave a clear solution. Slow cooling of this solution, followed by filtration gave 91 mg of yellow crystalline solid: m.p. 182°–183° C.; Anal. Calcd. for $C_{36}H_{40}N_4O_5 \cdot HCl \cdot H_2O$: C, 65.20, H, 6.54; N, 8.45. Found: C, 65.30; H, 6.28; N, 8.15.

EXAMPLE 8

3-(4,4-Diphenylpiperid-1-yl)-propanol 4,4-Diphenylpiperidine (40 g), 3-bromopropanol (24.7 g, Aldrich), powdered potassium carbonate (116.4 g) and approximately 1 g of potassium iodide (in 500 ml of a 1:1 mixture of dioxane and 1-butanol) were heated for about 48 hours under reflux and with vigorous stirring. After cooling, the mixture was filtered, and the filtrate was concentrated. The oily residue was taken up in ethyl acetate, and the solution was filtered again. Concentrating the filtrate to dryness yielded the product in the form of a yellowish, oily residue which slowly solidifies to a wax-like product (yield: 44.8 g). Hydrochloric acid in ether produced the hydrochloride (m.p.: 226° to 227° C.), which was recrystallized from 2-propanol.

Acetoacetic acid 3-(4,4-diphenylpiperidin-1-yl)propyl ester 23.6 g of 3-(4,4-diphenylpiperid-1-yl)-propanol were dissolved in 100 ml of absolute toluene, and 16 ml of a 50% strength solution of diketens in acetone were added with stirring. After standing for several days at room temperature (monitored by thin layer chromatography), the mixture was concentrated, and the residue was dried under high vacuum. The pale yellow, viscous oil which remains was employed without further purification for the next stage.

2,6-Dimethyl-4-(4-nitrophenyl)-1,4-dihydropyridine-3,5-dicarboxyylic acid [3-(4,4-diphenylpiperidin-1-yl)propyl] ester methyl ester A solution of methyl 3-aminocrotonate (265 mg, 2.3 mmol, 1.0 equiv), 4-nitrobenzaldehyde (348 mg, 2.3 mmol, 1.0 equiv), and acetoacetic acid 3-[4,4-diphenylpiperidin-1-yl)propyl]ester (872 mg, 2.3 mmol, 1.0 equiv) in isopropanol was refluxed under argon with stirring for 68 hours. Cooling and removal of solvent gave a residue, which was purified by flash chromatography ($SiO_2$, EtOAc-hexane, 1:1 and 1:2, followed by EtOAc) to afford 717 mg (51%) of yellow solid: $^1H$ NMR (300 MHz, $CDCl_3$) δ 1.73 (m, 2H), 2.22 (m, 2H), 2.30–2.51 (m, 8H), 2.34 (s, 3H), 2.35 (s, 3H), 3.63 (s, 3H), 4.05 (dr, J=2.1, 7.9 Hz, 2H), 5.06 (s, 1H), 5.73 (br s, 1H), 7.14 (m, 2H), 7.27 (m, 8H), 7.42 (dm, J=8.8 Hz, 2H), 8.06 (dm, J=8.8 Hz, 2H); $^{13}C$ NMR (75 MHz, $CDCl_3$) δ 15.30, 19.65, 26.32, 36.11, 39.88, 44.60, 50.60, 51.12, 55.34, 62.66, 102.99, 107.55, 123.39, 125.67, 127.12, 128.33, 128.65, 144.80, 144.93, 146.36, 147.50, 154.78, 166.91, 167.43; IR (neat) 1698.0, 1684.7, 1517.5, 1345.7 $cm^{-1}$; CIMS ($NH_3$) 610 $(M+1)^+$, 553, 338.

2,6-Dimethyl-4-(4-nitrophenyl)-1,4-dihydropyridine-3,5-dicarboxylic acid [3-(4,4-diphenylpiperidin-1-yl)propyl]ester methyl ester hydrochloride (Compound 8)

To a solution of 2,6-dimethyl-4-(4-nitrophenyl)-1,4-dihydro-pyridine-3,5-dicarboxylic acid [3-(4,4-diphenylpiperidine-1-yl)-propyl]ester methyl ester (710 mg, 1.16 mmol, 1.0 equiv) in EtOH (5 mL) was added a solution of HCl in ether (1.0M, 1.5 mL, 1.5 mmol, 1.3 equiv). The solvents were removed and the residue was dissolved in $CH_2Cl_2$. This solution was added dropwise to 25 mL of ether to afford, after filtration, 500 mg of yellow crystalline solid: m.p. 152°–153° C. Anal. Calcd. for $C_{36}H_9O_6 \cdot HCl$: C, 66.92; H, 6.24; N, 6.50. Found: C, 66.70; H, 5.99; N, 6.27

EXAMPLE 9

Protocol for the Determination of the Potency of $α_1$ Antagonists

The activity of compounds at the different human receptors was determined in vitro using cultured cell lines that selectively express the receptor of interest. These cell lines were prepared by transfecting the cloned cDNA or cloned genomic DNA or constructs containing both genomic DNA and cDNA encoding the human α-adrenergic, serotonin, histamine, and dopamine receptors as follows:

$α_{1A}$ Human Adrenergic Receptor: The entire coding region of α1A (1719 bp) (Sequence I.D. No. 1), including 150 basepairs of 5' untranslated sequence (5' UT) and 300 bp of 3' untranslated sequence (3' UT), was cloned into the BamHI and ClaI sites of the polylinker-modified eukaryotic expression vector pCEXV-3, called EXJ.HR. The construct involved the ligation of partial overlapping human lymphocyte genomic and hippocampal cDNA clones: 5' sequence were contained on a 1.2 kb SmaI-XhoI genomic fragment (the vector-derived BamHI site was used for subcloning instead of the internal insert-derived SmaI site) and 3' sequences were contained on an 1.3 kb XhoI-ClaI cDNA fragment (the ClaI site was from the vector polylinker). Stable cell lines were obtained by cotransfection with the plasmid α1A/EXJ (expression vector containing the α1A receptor gene) and the plasmid pGCcos3neo (plasmid containing the aminoglycoside transferase gene) into LM(tk⁻), CHO, and NIH3T3 cells, using calcium phosphate technique. The cells were grown, in a controlled environment (37° C., 5% $CO_2$), as monolayers in Dulbecco's modified Eagle's Medium (GIBCO, Grand Island, N.Y.) containing 25 mM glucose and supplemented with 10% bovine calf serum, 100 units/ml penicillin g, and 100 µg/ml streptomycin sulfate. Stable clones were then selected for resistance to the antibiotic G-418 (1 mg/ml), and membranes were harvested and assayed for their ability to bind [3H]prazosin as described below (see "Radioligand Binding assays").

$α_{1B}$ Human Adrenergic Receptor: The entire coding region of α1B (1563 bp) (Sequence I.D. No. 3), including 200 basepairs and 5' untranslated sequence (5' UT) and 600 bp of 3' untranslated sequence (3' UT), was cloned into the EcoRI site of pCEXV-3 eukaryotic expression vector. The construct involved ligating the full-length containing EcoRI brainstem cDNA fragment from λ ZapII into the expression vector. Stable cell lines were selected as described above.

Human $α_{1C}$ Adrenergic Receptor: The entire coding region of α1C (1401 bp) (Sequence I.D. No. 5), including 400 basepairs of 5' untranslated sequence (5' UT) and 200 bp of 3' untranslated sequence (3' UT), was cloned into the KpnI site of the polylinker-modified pCEXV-3-derived eukaryotic expression vector, EXJ.RH. The construct involved ligating three partial overlapping fragments: a 5' 0.6kb HincII genomic clone, a central 1.8 EcoRI hippocampal cDNA clone, and a 3' 0.6 Kb PstI genomic clone. The hippocampal cDNA fragment overlaps with the 5' and 3' genomic clones so that the HincII and PstI sites at the 5' and 3' ends of the cDNA clone, respectively, were utilized for ligation. This full-length clone was cloned into the KpnI site of the expression vector, using the 5' and 3' KpnI sites of the fragment, derived from vector (i.e., pBluescript) and 3'-untranslated sequences, respectively. Stable cell lines were selected as described above.

Radioligand Binding Assays: Transfected cells from culture flasks were scraped into 5 ml of 5 mM Tris-HCl, 5 mM EDTA, pH 7.5, and lysed by sonication. The cell lysates were centrifuged at 1000 rpm for 5 min at 4° C., and the supernatant was centrifuged at 30,000×g for 20 min at 4° C. The pellet was suspended in 50 mM Tris-HCl, 1 mM MgCl$_2$, and 0.1% ascorbic acid at pH 7.5. Binding of the α1 antagonist [$^3$H]prazosin (0.5 nM, specific activity 76.2 Ci/mmol) to membrane preparations of LM(tk-) cells was done in a final volume of 0.25 ml and incubated at 37° C. for 20 min. Nonspecific binding was determined in the presence of 10 μM phentolamine. The reaction was stopped by filtration through GF/B filters using a cell harvester. Inhibition experiments, routinely consisting of 7 concentrations of the tested compounds, were analyzed using a non-linear regression curve-fitting computer program to obtain Ki values.

α$_2$ Human Adrenergic Receptors: To determine the potency of α$_1$ antagonists at the α$_2$ receptors, LM(tk-) cell lines stably transfected with the genes encoding the α$_{2A}$, α$_{2B}$, and α$_{2C}$ receptors were used. The cell line expressing the α$_{2A}$ receptor is designated L-α$_{2A}$, and was deposited on Nov. 6, 1992 under ATCC Accession No. CRL 11180. The cell line expressing the α$_{2B}$ receptor is designated L-NGC-α$_{2B}$, and was deposited on Oct. 25, 1989 under ATCC Accession No. CRL10275. The cell line expressing the α$_{2C}$ receptor is designated L-α$_{2C}$, and was deposited on Nov. 6, 1992 under ATCC Accession No. CRL-11181. Cell lysates were prepared as described above (see Radioligand Binding Assays), and suspended in 25 mM glycylglycine buffer (pH 7.6 at room temperature). Equilibrium competition binding assay were performed using [3H]rauwolscine (0.5 nM), and nonspecific binding was determined by incubation with 10 μM phentolamine. The bound radioligand was separated by filtration through GF/B filters using a cell harvester.

Human Histamine H$_1$ Receptor: The coding sequence of the human histamine H$_1$ receptor, homologous to the bovine H$_1$ receptor, was obtained from a human hippocampal cDNA library, and was cloned into the eukaryotic expression vector pCEXV-3. The plasmid DNA for the H$_1$ receptor is designated pcEXV-H1, and was deposited on Nov. 6, 1992 under ATCC Accession No. 75346. This construct was transfected into COS-7 cells by the DEAE-dextran method. Cells were harvested after 72 hours and lysed by sonication in 5 mM Tris-HCl, 5 mM EDTA, pH 7.5. The cell lysates were centrifuged at 1000 rpm for 5 min at 4° C., and the supernatant was centrifuged at 30,000×g for 20 min. at 4° C. The pellet was suspended in 37.8 mM NaHPO$_4$, 12.2 mM KH$_2$PO$_4$, pH 7.5. The binding of the histamine H$_1$ antagonist [$^3$H]mepyramine (1 nM, specific activity: 24.8 Ci/mM) was done in a final volume of 0.25 ml and incubated at room temperature for 60 min. Nonspecific binding was determined in the presence of 10 μM mepyramine. The bound radioligand was separated by filtration through GF/B filters using a cell harvester.

Human Histamine H$_2$ Receptor: The coding sequence of the human H$_2$ receptor was obtained from a human placenta genomic library, and cloned into the cloning site of PCEXV-3 eukaryotic expression vector. The plasmid DNA for the H$_2$ receptor is designated pcEXV-H2, and was deposited on Nov. 6, 1992 under ATCC Accession No. 75346. This construct was transfected into COS-7 cells by the DEAE-dextran method. Cells were harvested after 72 hours and lysed by sonication in 5 mM Tris-HCl, 5 mM EDTA, pH 7.5. The cell lysates were centrifuged at 1000 rpm for 5 min at 4° C., and the supernatant was centrifuged at 30,000×g for 20 min at 4° C. The pellet was suspended in 37.8 mM NaHPO$_4$, 12.2 mM K2PO$_4$, pH 7.5. The binding of the histamine H$_2$ antagonist [$^3$H]tiotidine (5 nM, specific activity: 70 Ci/mM) was done in a final volume of 0.25 ml and incubated at room temperature for 60 min. Nonspecific binding was determined in the presence of 10 μM histamine. The bound radioligand was separated by filtration through GF/B filters using a cell harvester.

Human Serotonin Receptors:

5HT$_{1D\alpha}$, 5HT$_{1D\beta}$, 5HT$_1$, 5HT$_{1F}$ Receptors: The cell lysates of LM(tk-) clonal cell line stably transfected with the genes encoding each of these 5HT receptor-subtypes were prepared as described above. The cell line for the 5HT$_{1D\alpha}$ receptor, designated as Ltk-8-30-84, was deposited on Apr. 17, 1990, and accorded ATCC Accession No. CRL 10421. The cell for the 5HT$_{1D\beta}$ receptor, designated as Ltk-11, was deposited on Apr. 17, 1990, and accorded ATCC Accession No. CRL 10422. The cell line for the 5HT$_{1E}$ receptor, designated 5 HT$_{1E}$-7, was deposited on Nov. 6, 1991, and accorded ATCC Accession No. CRL 10913. The cell line for the 5HT$_{1F}$ receptor, designated L-5-HT$_{1F}$, was deposited on Dec. 27, 1991, and accorded ATCC Accession No. ATCC 10957. These preparations were suspended in 50 mM Tris-HCl buffer (pH 7.4 at 37° C.) containing 10 mM MgCl$_2$, 0.2 mM EDTA, 10 μM pargyline, and 0.1% ascorbate. The potency of α$_1$ antagonists was determined in competition binding assay by incubation for 30 minutes at 37° C. in the presence of 5 nM [3H]serotonin. Nonspecific binding was determined in the presence of 10 μM serotonin. The bound radioligand was separated by filtration through GF/B filters using a cell harvester.

Human 5HT$_2$ Receptors: The coding sequence of the human 5HT$_2$ receptor was obtained from a human brain cortex cDNA library, and cloned into the cloning site of pCEXV-3 eukaryotic expression vector. This construct was transfected into COS-7 cells by the DEAE-dextran method. Cells were harvested after 72 hours and lysed by sonication in 5 mM Tris-HCl, 5 mM EDTA, pH 7.5. This cell line was deposited with the ATCC on Oct. 31, 1989, designated as L-NGC-5HT$_2$, and was accorded ATCC Accession No. CRL 10287. The cell lysates were centrifuged at 1000 rpm for 5 minutes at 4° C., and the supernatant was centrifuged at 30,000×g for 20 minutes at 4° C. The pellet was suspended in 50 mM Tris-HCl buffer (pH 7.7 at room temperature) containing 10 mM MgSO$_4$, 0.5 mM EDTA, and 0.1% ascorbate. The potency of alpha-1 antagonists at 5HT2 receptors was determined in equilibrium competition binding assays using [3H]ketanserin (1 nM). Nonspecific binding was defined by the addition of 10 μM mianserin. The bound radioligand was separated by filtration through GF/B filters using a cell harvester.

Human Dopamine D2 Receptors: The potency of α$_1$ antagonists at the D2 receptor was determined using membrane preparations from COS-7 cells transfected with the gene encoding the human D2 receptor. The coding region for the human D2 receptor was obtained from a human striatum cDNA library, and cloned into the cloning site of PCDNA 1 eukariotic expression vector. The plasmid DNA for the D$_2$ receptor is designated pcEXV-D2, and was deposited on Nov. 6, 1992 under ATCC Accession No. ATC 75344. This construct was transfected into COS-7 cells by the DEAE-dextran method. Cells were harvested after 72 hours and lysed by sonication in 5 mM Tris-HCl, 5 mM EDTA, pH 7.5. The cell lysates were centrifuged at 1000 rpm for 5 minutes at 4° C., and the supernatant was centrifuged at 30,000×g for 20 minutes at 4° C. The pellet was suspended in 50 mM Tris-HCl (pH 7.4) containing 1 mM EDTA, 5 mM KCl, 1.5 mM $CaCl_2$, 4 mM $MgCl_2$, and 0.1% ascorbic acid. The cell lysates were incubated with [3H]spiperone (2 nM), using 10 μM (+)Butaclamol to determine nonspecific binding.

Other Dopamine receptors are prepared by known methods. ($D_3$: Sokoloff, P. et al., Nature, 347, 146 (1990), and deposited with the European Molecular Biological Laboratory (EMBL) Genbank as X53944; $D_4$: Van Tol, H. H. M., et al., Nature, 350, 610 (1991), and deposited with EMBL Genbank as X58497; $D_5$: Sunahara, R. K., et al., Nature, 350, 614 (1991), and deposited with EMBL Genbank as X58454-HU HD 5DR).

Determination of the Activity of α-Antagonists at Calcium Channels

The potency of α1 antagonists at calcium channels was determined in competition binding assays of [3H]nitrendipine to membrane fragments of rat cardiac muscle, essentially as described by Glossman and Ferry (Methods in Enzymology 109:513–550, 1985). Briefly, the tissue was minced and homogenized in 50 mM Tris-HCl (pH 7.4) containing 0.1 mM phenylmethylsulfonyl fluoride. The homogenates were centrifuged at 1000 g for 15 minutes, the resulting supernatant was centrifuged at 45,000 g for 15 minutes. The 45,000 g pellet was suspended in buffer and centrifuged a second time. Aliquots of membrane protein were incubated for 30 minutes at 37° C. in the presence of [3H]nitrendipine (1 nM), and nonspecific binding was determined in the presence of 10 μM nifedipine. The bound radioligand was separated by filtration through GF/B filters using a cell harvester.

EXAMPLE 10

Functional Properties of $\alpha_1$ Antagonists in the Human Prostate

The efficacy of $\alpha_1$ adrenergic antagonists for the treatment of benign prostatic hyperplasia (BPH) is related to their ability to elicit relaxation of prostate smooth muscle. An index of this efficacy can be obtained by determining the potency of $\alpha_1$ antagonists to antagonize the contraction of human prostatic tissue induced by an $\alpha_1$ agonist "in vitro". Furthermore, by comparing the potency of subtype selective $\alpha_1$ antagonists in binding assays using human $\alpha_1$ receptors with their potency to inhibit agonist-induced smooth muscle contraction, it is possible to determine which of the $\alpha_1$ adrenergic receptor subtypes is involved in the contraction of prostate smooth muscle.

Methods: Prostatic adenomas were obtained at the time of surgery from patients with symptomatic BPH. These were cut into longitudinal strips of 15 mm long and 2–4 mm wide, and suspended in 5 ml organ baths containing Krebs buffer (pH 7.4). The baths were maintained at 37° C. and continuously oxygenated with 5% $CO_2$ and 95% $O_2$. Isometric tension was measured with a Grass Instrument FTO3 force transducer interfaced with a computer. Tissue strips were contracted with varying concentrations of phenylephrine after incubating for 20 minutes in the absence and presence of at least three different concentrations of antagonist. Dose-response curves for phenylephrine were constructed, and the antagonist potency ($pA_2$) was estimated by the dose-ratio method. The concentration of some antagonists in the tissue bath was assessed by measuring the displacement of [3H] prazosin by aliquots of the bath medium, using membrane preparations of the cloned human $\alpha_{1C}$ receptor. This control was necessary to account for losses of antagonist due to adsorption to the tissue bath and/or metabolism during the time the antagonists were equilibrated with the prostate tissue.

Results:

Table 1 shows that the $pA_2$ values measured for a series of $\alpha_1$ antagonists in human prostate tissue correlate closely (r=0.76) with the corresponding $pK_i$ values measured in the $\alpha_{1C}$ receptor assays. In contrast, the human prostate $pA_2$ values correlate poorly with the $pK_i$ values measured at the $\alpha_{1A}$ (r=−0.06) and $\alpha_{1B}$ (r=−0.24) adrenergic receptors. (See FIG. 2 (Panels A–C). Thus, antagonists which are more potent at blocking the $\alpha_{1C}$ adrenergic receptor are more effective at blocking the contraction of the human prostate than antagonists which are more potent at the $\alpha_{1A}$ or $\alpha_{1B}$ adrenergic receptors. In addition, antagonists which are selective for the $\alpha_{1C}$ receptor will have a better therapeutic ratio than nonselective α antagonists.

With compound 11, the low $pA_2$ observed in the prostate may be attributed to tissue absorption or metabolism.

Table 2 illustrates the cross reactivity of $\alpha_1$ antagonists at other receptors such as $\alpha_{2A}$, $\alpha_{2B}$, $\alpha_{2C}$, histamine $H_1$, $H_2$, serotonin 5-$HT_{1D\alpha}$, 5-$HT_{1D\beta}$, 5-$HT_{1E}$, 5-$HT_{1F}$, 5-$HT_2$, and dopamine $D_2$. Only compounds 11, 8 and 2 have binding affinities which are greater than ten-fold higher at $\alpha_{1C}$ receptors than the binding affinities at other receptors.

Tables 3 and 4 show cross reactivity of alpha-1 agonists at cloned human receptors. Table 5 shows a comparison of alpha-1 agonist cross reactivity between human neuronal receptors and human alpha-1c receptor.

TABLE 1

COMPARISON OF THE BINDING POTENCY ($pK_i$) OF ALPHA-1 ANTAGONISTS IN CLONED HUMAN RECEPTORS AND THEIR POTENCY ($pA_2$) TO INHIBIT PROSTATE SMOOTH MUSCLE CONTRACTION

| Compound | Human Alpha-1 Adrenergic ($pK_i$) | | | Human Prostate (pA) |
|---|---|---|---|---|
| | α1A | α1B | α1C | |
| 1 Prazesin | 9.48 | 9.26 | 9.23 | 9.08 |
| 2 Compound 2 | 5.98 | 6.57 | 8.87 | 8.94 |
| 3 A 30380 | 7.49 | 7.86 | 8.52 | 8.72 |
| 4 5-Methyl-Urapidil | 7.79 | 6.77 | 8.35 | 8.38 |
| 5 Indoramin | 6.74 | 7.39 | 8.35 | 7.86 |
| 6 SKF-104856 | 8.48 | 7.50 | 6.60 | 7.66 |
| 7 Compound 7 | 6.82 | 7.18 | 8.42 | 7.63 |
| 8 Compound 8 | 6.52 | 7.07 | 8.48 | 7.46 |
| 9 Compound 9 | 6.12 | 6.76 | 7.83 | 7.41 |
| 10 Terazosin | 8.46 | 8.71 | 8.16 | 7.30 |
| 11 Compound 11 | 6.81 | 7.14 | 8.36 | 6.64 |

TABLE 2

| Compound | Alpha-1 Adrenergic | | | Alpha-2 Adrenergic | | | Histamine | | Serotonin | | | | | Dopamine | Calcium |
|---|---|---|---|---|---|---|---|---|---|---|---|---|---|---|---|
|  | $\alpha$1A | $\alpha$1B | $\alpha$1C | $\alpha$2a | s2b | $\alpha$2c | H1 | H2 | 5HT1D$\alpha$ | 5HT1D$\beta$ | 5HT1E | 5HT1F | 5HT2 | D2 | Channel |
| Terazosin | 8.46 | 8.71 | 8.16 | 6.26 | 7.51 | 6.64 | 4.00 | 5.04 | <6.0 | <6.0 | <5.0 | <5.0 | <5.0 | <5.0 | 5.19 |
| Prazosin | 9.48 | 9.26 | 9.23 | 6.76 | 7.64 | 7.65 | 4.00 | 5.19 | <5.0 | <5.0 | ND | ND | <6.0 | <5.0 | 4.57 |
| 5-Methyl-urapidil | 7.79 | 6.77 | 8.35 | 6.63 | 7.38 | 6.88 | 5.16 | 4.47 | 7.30 | 6.82 | ND | ND | <6.0 | <5.0 | ND |
| Indoramin | 6.74 | 7.39 | 8.35 | 4.94 | 5.72 | 5.22 | 7.37 | 5.63 | <6.0 | <6.0 | <5.0 | <5.0 | <7.0 | <8.0 | 4.53 |
| Compound 11 | 6.81 | 7.14 | 8.36 | 6.86 | 6.90 | 6.92 | 5.74 | 7.45 | <6.0 | <6.0 | <5.0 | <5.0 | <7.0 | <6.0 | 5.18 |
| A-30360 | 7.49 | 7.86 | 8.52 | 6.69 | 6.37 | 6.23 | 6.03 | 5.77 | <6.0 | <6.0 | <5.0 | <5.0 | <8.0 | <9.0 | 5.26 |
| Compound 7 | 6.82 | 7.18 | 8.42 | 6.19 | 6.07 | 6.09 | 7.59 | 6.02 | <6.0 | <5.0 | <5.0 | <5.0 | <6.0 | <7.0 | 4.79 |
| Compound 9 | 6.12 | 6.76 | 7.83 | 5.80 | 5.89 | 5.90 | 7.29 | 5.44 | <6.0 | <6.0 | <5.0 | <5.0 | <7.0 | <7.0 | 4.44 |
| SKF-104858 | 8.48 | 7.50 | 7.60 | 7.30 | 8.49 | 7.60 | 5.59 | 5.84 | <7.0 | <7.0 | <6.0 | <7.0 | <6.0 | <7.0 | 4.68 |
| S-Niguldipine | 6.72 | 7.07 | 8.75 | 6.19 | 5.24 | 6.43 | 6.78 | 6.24 | ND | ND | ND | ND | <7.0 | <7.0 | 8.04 |
| Compound 8 | 6.52 | 7.07 | 8.48 | 5.99 | 6.12 | 5.77 | 6.67 | 6.11 | <6.0 | <5.0 | <5.0 | <5.0 | <7.0 | <6.0 | 6.87 |
| Compound 2 | 5.98 | 6.57 | 8.87 | 5.48 | 5.93 | 5.88 | 7.16 | 7.48 | <7.0 | <6.0 | <5.0 | <5.0 | <6.0 | <7.0 | 6.13 |

ND = Not Determined

TABLE 3

CROSS REACTIVITY OF ALPHA-1 ANTAGONISTS AT CLONED HUMAN RECEPTORS

| pKi Compound | Alpha-1 Adrenergic | | | | | | Alpha-2 Adrenergic | | | | | | Histamine | | | | Calcium | |
|---|---|---|---|---|---|---|---|---|---|---|---|---|---|---|---|---|---|---|
| | a1A MEAN | SEM | a1B MEAN | SEM | a1C MEAN | SEM | a2a MEAN | SEM | a2b MEAN | SEM | a2c MEAN | SEM | H1 MEAN | SEM | H2 MEAN | SEM | Channel MEAN | SEM |
| Terazosin | 8.46 | 0.04 | 8.71 | 0.04 | 8.16 | 0.02 | 6.26 | 0.11 | 7.51 | 0.08 | 6.64 | 0.03 | 4.00 | | 5.04 | 0.27 | 5.19 | |
| Prazosin | 9.48 | 0.11 | 9.26 | 0.13 | 9.23 | 0.08 | 6.76 | 0.09 | 7.64 | 0.19 | 7.65 | 0.07 | 4.00 | | 5.19 | 0.20 | 4.57 | |
| 5-Methylurapidil | 7.79 | 0.10 | 6.77 | 0.10 | 8.35 | 0.10 | 6.63 | 0.07 | 7.38 | 0.04 | 6.88 | 0.03 | 5.16 | 0.11 | 4.47 | 0.09 | ND | |
| Indoramin | 6.74 | 0.08 | 7.39 | 0.08 | 8.35 | 0.08 | 4.94 | 0.17 | 5.72 | 0.15 | 5.22 | 0.05 | 7.37 | 0.13 | 5.63 | 0.08 | 4.53 | |
| Compound 11 | 6.81 | 0.06 | 7.14 | 0.17 | 8.36 | 0.17 | 6.86 | 0.01 | 6.90 | 0.05 | 6.92 | 0.05 | 5.74 | 0.01 | 7.45 | 0.00 | 5.18 | |
| A-30360 | 7.49 | 0.10 | 7.86 | 0.10 | 8.52 | 0.10 | 6.69 | 0.07 | 6.37 | 0.04 | 6.23 | 0.03 | 6.03 | 0.11 | 5.77 | 0.09 | 5.26 | |
| Compound 7 | 6.82 | 0.03 | 7.18 | 0.11 | 8.42 | 0.11 | 6.19 | 0.01 | 6.07 | 0.01 | 6.09 | 0.01 | 7.59 | 0.12 | 6.02 | 0.01 | 4.79 | |
| Compound 9 | 6.12 | 0.18 | 6.76 | 0.28 | 7.83 | 0.03 | 5.80 | | 5.69 | | 5.90 | | 7.29 | 0.08 | 5.44 | 0.09 | 4.00 | |
| SKF-104856 | 8.48 | 0.05 | 7.50 | 0.23 | 7.60 | 0.23 | 7.30 | 0.61 | 8.49 | 0.44 | 7.60 | 0.23 | 5.59 | 0.07 | 5.84 | 0.04 | 4.68 | |
| S-Niguldipine | 6.72 | 0.08 | 7.07 | 0.12 | 8.75 | 0.12 | 6.19 | | 5.24 | | 6.43 | 0.11 | 6.78 | 0.03 | 6.24 | 0.07 | 8.04 | 0.06 |
| Compound 8 | 6.52 | 0.06 | 7.07 | 0.04 | 8.48 | 0.04 | 5.99 | 0.05 | 6.12 | 0.03 | 5.77 | 0.09 | 6.67 | 0.09 | 6.11 | 0.05 | 6.87 | 0.12 |
| Compound 2 | 5.98 | 0.07 | 6.57 | 0.12 | 8.87 | 0.12 | 5.48 | 0.12 | 5.93 | 0.04 | 5.88 | 0.13 | 7.16 | 0.04 | 7.48 | 0.06 | 6.13 | 0.01 |

Comparison of Alpha-1 Antagonist Crossreactivity Between Human Neuronal Receptors and Human Alpha-1c

| pKi Compound | 5HT1Da | 5HT1Db | 5HT1E | 5HT1F | 5HT2 | D2 | Ca Chann |
|---|---|---|---|---|---|---|---|
| Terazosin | 6.00 | 6.00 | 5.00 | 5.00 | 5.00 | 5.00 | 5.19 |
| Prazosin | 5.00 | 5.00 | ND | ND | 6.00 | 5.00 | 4.57 |
| 5-Methylurapidil | 7.30 | 6.82 | ND | ND | 6.00 | 5.00 | ND |
| Indoramin | 6.00 | 6.00 | 5.00 | 5.00 | 7.00 | 8.00 | 4.53 |
| Compound 11 | 6.00 | 6.00 | 5.00 | 5.00 | 7.00 | 6.00 | 5.18 |
| A-30360 | 6.00 | 6.00 | 5.00 | 5.00 | 8.00 | 9.00 | 5.26 |
| Compound 7 | 6.00 | 5.00 | 5.00 | 6.00 | 6.00 | 7.00 | 4.79 |
| Compound 9 | 6.00 | 6.00 | 5.00 | 5.00 | 7.00 | 7.00 | 4.00 |
| SKF-104858 | 7.00 | 7.00 | 6.00 | 7.00 | 6.00 | 7.00 | 4.68 |
| S-Niguldipine | ND | ND | ND | ND | 7.00 | 7.00 | 8.04 |
| Compound 8 | 6.00 | 5.00 | 5.00 | 5.00 | 7.00 | 6.00 | 6.87 |
| Compound 2 | 7.00 | 6.00 | 5.00 | 5.00 | 6.00 | 7.00 | 6.13 |

ND = Not Determined
As used herein, SEM means the standard error of the mean.

TABLE 4

CROSS REACTIVITY OF ALPHA-1 ANTAGONISTS AT CLONED HUMAN RECEPTORS

| pKi Compound | Alpha-1 Adrenergic | | | | | | Alpha-2 Adrenergic | | | | | | Histamine | | | | Calcium Channel | |
|---|---|---|---|---|---|---|---|---|---|---|---|---|---|---|---|---|---|---|
| | a1A MEAN | SEM | a1B MEAN | SEM | a1C MEAN | SEM | a2a MEAN | SEM | a2b MEAN | SEM | a2c MEAN | SEM | H1 MEAN | SEM | H2 MEAN | SEM | MEAN | SEM |
| Terazosin | 3 | 0.31 | 2 | 0.17 | 7 | 0.31 | 550 | 123 | 31 | 5 | 226 | 15 | 100000 | | 9120 | 4222 | 6457 | |
| Prazosin | 0.33 | 0.07 | 0.55 | 0.14 | 0.59 | 0.10 | 174 | 33 | 23 | 8 | 22 | 3 | 100000 | | 6457 | 2383 | 26915 | |
| 5-Methylurapidil | 16 | 3 | 170 | 35 | 4 | 0.92 | 234 | 35 | 42 | 4 | 132 | 9 | 6918 | 1548 | 33884 | 6342 | | |
| Indoramin | 182 | 31 | 41 | 7 | 4 | 0.75 | 11482 | 3719 | 1905 | 556 | 6026 | 776 | 43 | 11 | 2344 | 384 | 29512 | |
| Compound 11 | 155 | 20 | 72 | 23 | 4 | 1.41 | 136 | 3 | 126 | 14 | 120 | 13 | 1620 | 41 | 35 | 0.08 | 6607 | |
| A-30360 | 32 | 7 | 14 | 3 | 3 | 0.62 | 204 | 30 | 427 | 38 | 589 | 39 | 933 | 209 | 1698 | 318 | 5495 | |
| Compound 7 | 151 | 10 | 66 | 15 | 4 | 0.85 | 646 | 15 | 851 | 19 | 813 | 19 | 26 | 6 | 955 | 22 | 16218 | |
| Compound 9 | 759 | 257 | 174 | 83 | 15 | 0.99 | 1585 | 0 | 2042 | | 1259 | | 51 | 9 | 3631 | 680 | 10000 | |
| SKF-104856 | 3 | 0.36 | 32 | 13 | 25 | 10.33 | 50 | 38 | 3 | 2 | 25 | 10 | 2570 | 383 | 1445 | 127 | 20893 | |
| S-Niguldipine | 191 | 32 | 85 | 21 | 2 | 0.43 | 646 | | 5754 | | 372 | 83 | 166 | 11 | 575 | 86 | 9 | 1 |
| Compound 8 | 302 | 39 | 85 | 7 | 3 | 0.29 | 1023 | 111 | 759 | 51 | 1698 | 318 | 214 | 40 | 776 | 84 | 135 | 33 |
| Compound 2 | 1047 | 156 | 269 | 65 | 1 | 0.33 | 3311 | 799 | 1175 | 103 | 1318 | 341 | 69 | 6 | 33 | 4 | 741 | 17 |

| Ki (nM) Compound | 5HT1Da | 5HT1Db | 5HT1E | 5HT1F | 5HT2 | D2 | Ca Chann |
|---|---|---|---|---|---|---|---|
| Terazosin | 1000 | 1000 | 10000 | 10000 | 10000 | 10000 | 6457 |
| Prazosin | 10000 | 10000 | ND | ND | 1000 | 10000 | 26915 |
| 5-Methylurapidil | 50 | 151 | ND | ND | 100 | 10000 | |
| Indoramin | 1000 | 1000 | 10000 | 10000 | 100 | 10 | 29512 |
| Compound 11 | 1000 | 1000 | 10000 | 10000 | 100 | 1000 | 6607 |
| A-30360 | 1000 | 1000 | 10000 | 10000 | 10 | 1 | 5495 |
| Compound 7 | 1000 | 10000 | 10000 | 10000 | 1000 | 100 | 16218 |
| Compound 9 | 1000 | 1000 | 10000 | 10000 | 100 | 100 | 100000 |
| SKF-104856 | 100 | 100 | 1000 | 100 | 1000 | 100 | 20893 |
| S-Niguldipine | ND | ND | ND | ND | 100 | 100 | 9 |
| Compound 8 | 1000 | 10000 | 10000 | 10000 | 100 | 1000 | 135 |
| Compound 2 | 100 | 1000 | 10000 | 10000 | 1000 | 100 | 741 |

ND = Not Determined

TABLE 5

COMPARISON OF ALPHA-1 ANTAGONIST CROSSREACTIVITY BETWEEN HUMAN
NEURONAL RECEPTORS AND HUMAN ALPHA-1C RECEPTOR
(ANTAGONIST Ki ALPHA-1C NEURONAL RECEPTOR)
(ANTAGONIST Ki ALPHA-1C ADRENERGIC RECEPTOR)

| Compound | Alpha-1 Adrenergic | | | | | | Alpha-2 Adrenergic | | | | | | Histamine | | | | Calcium Channel | |
|---|---|---|---|---|---|---|---|---|---|---|---|---|---|---|---|---|---|---|
| | a1A MEAN | SEM | a1B MEAN | SEM | a1C MEAN | SEM | a2a MEAN | SEM | a2b MEAN | SEM | a2c MEAN | SEM | H1 MEAN | SEM | H2 MEAN | SEM | MEAN | SEM |
| Terazosin | 1 | 0 | 0 | 0 | | 1 | 79 | 18 | 4 | 1 | 33 | 2 | 14454 | | 1318 | 610 | 933 | |
| Prazosin | 1 | 0 | 1 | 0 | | 1 | 295 | 55 | 39 | 14 | 38 | 6 | 169824 | | 10965 | 4046 | 45709 | |
| 5-Methylurapidil | 4 | 1 | 38 | 8 | | 1 | 52 | 8 | 9 | 1 | 30 | 2 | 1549 | 347 | 7586 | 1420 | | |
| Indoramin | 41 | 7 | 9 | 2 | | 1 | 2570 | 833 | 427 | 125 | 1349 | 174 | 10 | 2 | 525 | 88 | 6607 | |
| Compound 11 | 35 | 5 | 17 | 5 | | 1 | 32 | 1 | 29 | 3 | 28 | 3 | 417 | 9 | 8 | 0 | 1514 | |
| A-30360 | 11 | 2 | 5 | 1 | | 1 | 68 | 10 | 141 | 12 | 195 | 13 | 309 | 69 | 562 | 105 | 1820 | |
| Compound 7 | 40 | 3 | 17 | 4 | | 1 | 170 | 4 | 224 | 5 | 214 | 5 | 7 | 2 | 251 | 6 | 4266 | |
| Compound 9 | 51 | 17 | 12 | 6 | | 1 | 107 | 0 | 138 | 0 | 85 | 0 | 3 | 1 | 245 | 46 | 6761 | |
| SKF-104856 | 0 | 0 | 1 | 1 | | 1 | 2 | 2 | 0 | 0 | 1 | 0 | 102 | 15 | 58 | 5 | 832 | |
| S-Niguldipine | 107 | 18 | 48 | 12 | | 1 | 363 | 0 | 3236 | 0 | 209 | 47 | 93 | 6 | 324 | 48 | 5 | 1 |
| Compound 8 | 91 | 12 | 26 | 2 | | 1 | 309 | 34 | 229 | 15 | 513 | 96 | 65 | 12 | 234 | 25 | 41 | 10 |
| Compound 2 | 776 | 116 | 200 | 48 | | 1 | 2455 | 593 | 871 | 77 | 977 | 253 | 51 | 5 | 25 | 3 | 550 | 13 |

ALPHA-1c SELECTIVITY

| Compound | 5HT1Da | 5HT1Db | 5HT1E | 5HT1F | 5HT2 | D2 | Ca Chann |
|---|---|---|---|---|---|---|---|
| Terazosin | 145 | 145 | 1445 | 1445 | 1445 | 1445 | 933 |
| Prazosin | 16982 | 16982 | ND | ND | 1698 | 16982 | 45709 |
| 5-Methylurapidil | 11 | 34 | ND | ND | 224 | 2239 | |
| Indoramin | 224 | 224 | 2239 | 2239 | 22 | 2 | 6607 |
| Compound 11 | 229 | 229 | 2291 | 2291 | 23 | 229 | 1514 |
| A-30360 | 331 | 331 | 3311 | 3311 | 3 | 0 | 1820 |
| Compound 7 | 263 | 2630 | 2630 | 2630 | 263 | 26 | 4266 |
| Compound 9 | 68 | 68 | 676 | 676 | 7 | 7 | 6761 |
| SKF-104856 | 4 | 4 | 40 | 4 | 40 | 4 | 5 |
| S-Niguldipine | ND | ND | ND | ND | 56 | 56 | 41 |
| Compound 8 | 302 | 3020 | 3020 | 3020 | 30 | 302 | 550 |
| Compound 2 | 74 | 741 | 7413 | 7413 | 741 | 74 | |

ND = Not Determined

EXAMPLE 11

Functional Properties of $\alpha_1$ Antagonists on Rat Orthostatic Hypertension We have identified a large series of compounds (well over 150 compounds, data not shown) which exemplify the hereinabove described properties of antagonists highly selective for the $\alpha_{1C}$ adrenergic receptor. That is, these compounds are highly selective Alpha 1c antagonists which have less than 10 fold the affinity at cloned human Alpha 1a, Alpha 1b, Alpha 2a, Alpha 2b, Alpha 2c, Histamine H1, Dopamine D2 and Serotonin receptors. In addition, these compounds have 10 fold lower affinity at calcium channels (data not shown). we designated five of these highly selective antagonists for the $\alpha_{1C}$ adrenergic receptor as drugs 21–25 and used them to further characterize highly selective antagonists for the $\alpha_{1C}$ adrenergic receptor.

In addition, a number of these selective alpha 1c antagonists are potent at inhibiting the phenylephrine stimulated contraction of human prostate as described in Example 10. This is a well established protocol for evaluation the efficacy of drugs which may be useful for the treatment of BFH.

In addition, we have examined a number of selective alpha 1c antagonists in an in vivo canine prostate model (Felson, D., et al., *J. Urol.*, 141, 1230–1233 (1989))which is a well characterized model for evaluating the efficacy of BPH drugs (data not shown). In this model, selective alpha 1c antagonists increase urethral pressure at doses which do not produce significant decreases in canine blood pressure. In contrast, nonselective alpha 1 antagonists do not have as large a separation between the effects on urethral pressure and the effects on blood pressure. These observations support our premise that a selective alpha 1c antagonist will have a better safety profile than a nonselective alpha 1 antagonist. We have further characterized selective alpha 1c antagonists in a rat orthostatic hypotension model. This model gives information on the vascular effects of drugs which may be indicative of their ability to produce dizziness in patients (Hieble, J. P., et al., *Cardiovascular Pharmacology*, 15, 845 (1990)). Our objective was to characterize the effects of selective alpha 1c antagonists on rat orthostatic hypotension and contrast the results with those obtained using nonselective alpha 1 antagonists.

METHODS

Rat Orthostatic Hypotension Model

Adult male Sprague-Dawley normotensive rats were anesthetized with sodium pentobarbital (45 mg/kg, i.v.). The femoral vein and artery of the right hindlimb were cannulated for drug administration and blood pressure monitoring, respectively. Heart rate was determined by a cardiotachometer triggered by the blood pressure pulse. The rats were secured in the supine position to a board that could be tilted 90 degrees. When blood pressure and heart rate had stabilized, the rats were subjected to a 90 degree vertical (head up) tilt for 60 seconds. Changes in blood pressure and heart rate from pre-tilt levels were monitored continuously. The rats were returned to the supine position and blood pressure and heart rate were allowed to stabilize. Either an antagonist selective for the $\alpha_{1C}$ adrenergic receptor (designated drug 21, 22, 23, 24 or 25), an antagonist nonselective for the $\alpha_{1C}$ adrenergic receptor (Prazosin or Terazosin) or saline was then administered through venous cannula, either as an i.v. bolus or as an infusion. When blood pressure had stabilized, the rats were subjected to a second tilt and blood pressure and heart rate were recorded as described above. Most saline treated rats typically exhibit a greater ability to return their blood pressure toward pre-tilt levels during the second tilt. Data from the second tilt are used in statistical analysis.

RESULTS

Table 6 shows that while nonselective alpha 1 antagonists produce significant effects on orthostatic hypotension, selective alpha 1c antagonists do not produce significant effects. More specifically, Prazosin and Terazosin consistently cause orthostasis at the lowest dose (10 ug/kg) and, in some rats, in a dose-dependent manner. Drug 21 causes orthostasis only at the highest dose (1000 ug/kg) in 2 out of 4 rats, while the other antagonists selective for the $\alpha_{1C}$ adrenergic receptor caused no orthostasis at the highest dose. Placebo and 22, 23, 24, 25 did not induce orthostasis at any dose. Taken all together, this is a positive result since it is believed that orthostatic hypotension contributes to the dizziness observed clinically with nonselective alpha 1 antagonists. This further supports our premise that a selective alpha 1c antagonist will have a better safety profile than a nonselective alpha 1 antagonist.

TABLE 6

| | | Summary of Studies on Drug Effects on Orthostasis | | | | | | |
|---|---|---|---|---|---|---|---|---|
| | | Dose 1 10 ug/kg | | Dose 2 100 ug/kg | | Dose 3 1000 ug/kg | | |
| Drug | n | orthostatic fall in BP | BP fall | orthostatic fall in BP | BP fall | orthostatic fall in BP | BP fall | Notes |
| Placebo (DMSO) | 3 | – | – | – | – | – | – | |
| Prezosin | 4 | + | + | ++ or +++ | ++ | ++ or +++ | +++ | |
| Terazosin | 2 | + | + | ++ or +++ | ++ | ++ or +++ | +++ | |
| 21 | 4 | – | + | – | ++ | +/– | +++ | (+ in 2/4) |
| 22 | 3 | – | + | – | ++ | – | +++ | |
| 23 | 6 | – | – | – | – | – | + | |
| 24 | 6 | – | – | – | +/– | – | + | |
| 25 | 4 | – | – | +/– | – | – | – | (+ in 1/4) |

+ and – mean positive or negative findings, respectively
+, ++ and +++ are relative to doses of the same drug but not compared to other drugs
+/– positive findings found in some rats

What is claimed is:

1. A method of treating benign prostatic hyperplasia in a subject which comprises administering to the subject a therapeutically effective amount of a compound which:
   a. binds to a human $\alpha_{1C}$ adrenergic receptor with a binding affinity greater than 20-fold higher than the binding affinity with which the compound binds to a human $\alpha_{1A}$ adrenergic receptor, a human $\alpha_{1B}$ adrenergic receptor, and a human histamine $H_1$ receptor; and
   b. binds to a human $\alpha_2$ adrenergic receptor with a binding affinity which is greater than 20-fold lower than the binding affinity with which the compound binds to such $\alpha_{1C}$ adrenergic receptor.

2. The method of claim 1, wherein the compound (a) binds to a human $\alpha_{1C}$ adrenergic receptor with a binding affinity greater than 50-fold higher than the binding affinity with which the compound binds to a human $\alpha_{1A}$ adrenergic receptor, a human $\alpha_{1B}$ adrenergic receptor, and a human histamine $H_1$ receptor, and (b) binds to a human $\alpha_2$ adrenergic receptor with a binding affinity which is greater than 50-fold lower than the binding affinity with which the compound binds to such $\alpha_{1C}$ adrenergic receptor.

3. The method of claim 2, wherein the compound (a) binds to a human $\alpha_{1C}$ adrenergic receptor with a binding affinity greater than 100-fold higher than the binding affinity with which the compound binds to a human $\alpha_{1A}$ adrenergic receptor, a human $\alpha_{1B}$ adrenergic receptor, and a human histamine $H_1$ receptor, and (b) binds to a human $\alpha_2$ adrenergic receptor with a binding affinity which is greater than 100-fold lower than the binding affinity with which the compound binds to such $\alpha_{1C}$ adrenergic receptor.

4. The method of claim 3, wherein the compound (a) binds to a human $\alpha_{1C}$ adrenergic receptor with a binding affinity greater than 300-fold higher than the binding affinity with which the compound binds to a human $\alpha_{1A}$ adrenergic receptor, a human $\alpha_{1B}$ adrenergic receptor, and a human histamine $H_1$ receptor, and (b) binds to a human $\alpha_2$ adrenergic receptor with a binding affinity which is greater than 300-fold lower than the binding affinity with which the compound binds to such $\alpha_{1C}$ adrenergic receptor.

5. The method of claim 1, 2, 3 or 4, wherein the compound additionally binds to a calcium channel with a binding affinity which is greater than ten-fold lower than the binding affinity with which the compound binds to the $\alpha_{1C}$ adrenergic receptor.

6. The method of claim 1, 2, 3 or 4, wherein the compound binds to a calcium channel with a binding affinity which is greater than 20-fold lower than the binding affinity with which the compound binds to the $\alpha_{1C}$ adrenergic receptor.

7. The method of claim 1, 2, 3 or 4, wherein the compound binds to a calcium channel with a binding affinity which is greater than 50-fold lower than the binding affinity with which the compound binds to the $\alpha_{1C}$ adrenergic receptor.

8. The method of claim 1, 2, 3 or 4, wherein the compound binds to a calcium channel with a binding affinity which is greater than 100-fold lower than the binding affinity with which the compound binds to the $\alpha_{1C}$ adrenergic receptor.

9. The method of claim 1, 2, 3 or 4, wherein the compound binds to a calcium channel with a binding affinity which is greater than 300-fold lower than the binding affinity with which the compound binds to the $\alpha_{1C}$ adrenergic receptor.

10. The method of claim 1, 2, 3 or 4, wherein the compound additionally binds to a human dopamine $D_2$ or human $H_2$ receptor with a binding affinity which is greater than ten-fold lower than the binding affinity with which the compound binds to the $\alpha_{1C}$ adrenergic receptor.

11. The method of claim 1, 2, 3 or 4, wherein the compound binds to a human dopamine $D_2$ or human $H_2$ receptor with a binding affinity which is greater than 20-fold lower than the binding affinity with the compound binds to the $\alpha_{1C}$ adrenergic receptor.

12. The method of claim 1, 2, 3 or 4, wherein the compound binds to a human dopamine $D_2$ or human $H_2$ receptor with a binding affinity which is greater than 50-fold lower than the binding affinity with which the compound binds to the $\alpha_{1C}$ adrenergic receptor.

13. The method of claim 1, 2, 3 or 4, wherein the compound binds to a human dopamine $D_2$ or human $H_2$ receptor with a binding affinity which is greater than 100-fold lower than the binding affinity with which the compound binds to the $\alpha_{1C}$ adrenergic receptor.

14. The method of claim 1, 2, 3 or 4, wherein the compound binds to a human dopamine $D_2$ or human $H_2$ receptor with a binding affinity which is greater than 300-fold lower than the binding affinity with which the compound binds to the $\alpha_{1C}$ adrenergic receptor.

15. The method of claim 1, 2, 3 or 4, wherein the compound additionally binds to any serotonin receptor with a binding affinity which is greater than ten-fold lower than the binding affinity with which the compound binds to the $\alpha_{1C}$ adrenergic receptor.

16. The method of claim 1, 2, 3 or 4, wherein the compound binds to any serotonin receptor with a binding affinity which is greater than 20-fold lower than the binding affinity with which the compound binds to the $\alpha_{1C}$ adrenergic receptor.

17. The method of claim 1, 2, 3 or 4, wherein the compound binds to any serotonin receptor with a binding affinity which is greater than 50-fold lower than the binding affinity with which the compound binds to the $\alpha_{1C}$ adrenergic receptor.

18. The method of claim 1, 2, 3 or 4, wherein the compound binds to any serotonin receptor with a binding affinity which is greater than 100-fold lower than the binding affinity with which the compound binds to the $\alpha_{1C}$ adrenergic receptor.

19. The method of claim 1, 2, 3 or 4, wherein the compound binds to any serotonin receptor with a binding affinity which is greater than 300-fold lower than the binding affinity with which the compound binds to the $\alpha_{1C}$ adrenergic receptor.

20. The method of claim 1, 2, 3 or 4, wherein the compound additionally binds to a dopamine $D_3$, $D_4$, or $D_5$ receptor with a binding affinity which is greater than ten-fold lower than the binding affinity with which the compound binds to the $\alpha_{1C}$ adrenergic receptor.

21. The method of claim 1, 2, 3 or 4, wherein the compound binds to a dopamine $D_3$, $D_4$, or $D_5$ receptor with a binding affinity which is greater than 20-fold lower than the binding affinity with which the compound binds to the $\alpha_{1C}$ adrenergic receptor.

22. The method of claim 1, 2, 3 or 4, wherein the compound binds to a dopamine $D_3$, $D_4$, or $D_5$ receptor with a binding affinity which is greater than 50-fold lower than the binding affinity with which the compound binds to the $\alpha_{1C}$ adrenergic receptor.

23. The method of claim 1, 2, 3 or 4, wherein the compound binds to a dopamine $D_3$, $D_4$, or $D_5$ receptor with a binding affinity which is greater than 100-fold lower than the binding affinity with which the compound binds to the $\alpha_{1C}$ adrenergic receptor.

24. The method of claim 1, 2, 3 or 4, wherein the compound binds to a dopamine $D_3$, $D_4$, or $D_5$ receptor with a binding affinity which is greater than 300-fold lower than the binding affinity with which the compound binds to the $\alpha_{1C}$ adrenergic receptor.

25. A method of claims 1, 2, 3 or 4, wherein the compound additionally does not cause an orthostatic fall in blood pressure at dosages effective to alleviate benign prostatic hyperplasia.

26. The method of claim 25, wherein the compound additionally does not cause an orthostatic fall in blood pressure in rats at a dosage of 10 micrograms of compound per kilogram of rat.

27. The method of claim 1, wherein the compound has the structure:

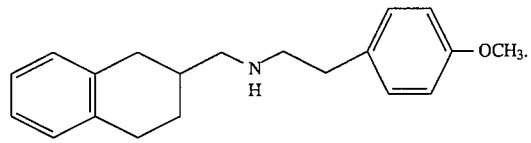

28. The method of claim 1 or 2, wherein the compound has the structure:

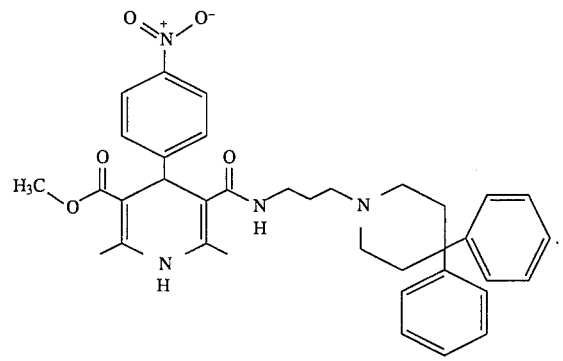

29. The method of claim 1, wherein the compound has the structure:

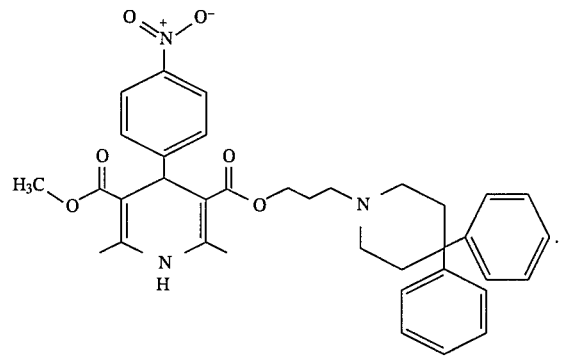

30. The method of claim 1, wherein the compound has the structure:

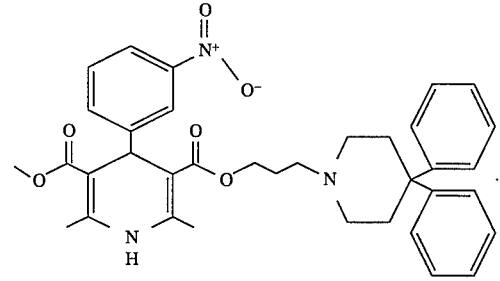

31. A method of inhibiting contraction of prostate tissue which comprises contacting the prostate tissue with an effective contraction-inhibiting amount of a compound which:

a. binds to a human $\alpha_{1C}$ adrenergic receptor with a binding affinity greater than 20-fold higher than the binding affinity with which the compound binds to a human adrenergic receptor, a human $\alpha_{1B}$ adrenergic receptor, and a human histamine $H_1$ receptor; and b. binds to a human $\alpha_2$ adrenergic receptor with a binding affinity which is greater than 20-fold lower than the binding affinity with which the compound binds to such $\alpha_{1C}$ adrenergic receptor.

32. The method of claim 31, wherein the compound (a) binds to a human $\alpha_{1C}$ adrenergic receptor with a binding affinity greater than 50-fold higher than the binding affinity with which the compound binds to a human $\alpha_{1A}$ adrenergic receptor, a human $\alpha_{1B}$ adrenergic receptor, and a human histamine $H_1$ receptor, and (b) binds to a human $\alpha_2$ adrenergic receptor with a binding affinity which is greater than 50-fold lower than the binding affinity with which the compound binds to such $\alpha_{1C}$ adrenergic receptor.

33. The method of claim 32, wherein the compound (a) binds to a human $\alpha_{1C}$ adrenergic receptor with a binding affinity greater than 100-fold higher than the binding affinity with which the compound binds to a human $\alpha_{1A}$ adrenergic receptor, a human $\alpha_{1B}$ adrenergic receptor, and a human histamine $H_1$ receptor, and (b) binds to a human $\alpha_2$ adrenergic receptor with a binding affinity which is greater than 100-fold lower than the binding affinity with which the compound binds to such $\alpha_{1C}$ adrenergic receptor.

34. The method of claim 33, wherein the compound (a) binds to a human $\alpha_{1C}$ adrenergic receptor with a binding affinity greater than 300-fold higher than the binding affinity with which the compound binds to a human $\alpha_{1A}$ adrenergic receptor, a human $\alpha_{1B}$ adrenergic receptor, and a human histamine $H_1$ receptor, and (b) binds to a human $\alpha_2$ adrenergic receptor with a binding affinity which is greater than 300-fold lower than the binding affinity with which the compound binds to such $\alpha_{1C}$ adrenergic receptor.

35. A method of claim 31, wherein the compound additionally does not cause an orthostatic fall in blood pressure at dosages effective to alleviate benign prostatic hyperplasia.

36. The method of claim 35, wherein the compound additionally does not cause an orthostatic fall in blood pressure in rats at a dosage of 10 micrograms of compound per kilogram of rat.

* * * * *

UNITED STATES PATENT AND TRADEMARK OFFICE
CERTIFICATE OF CORRECTION

PATENT NO. : 5,578,611
DATED : November 26, 1996
INVENTOR(S) : Charles Gluchowski, Carlos C. Forray, George Chiu, Theresa A. Branchek, John M. Wetzel, Paul R. Hartig It is certified that error appears in the above-identified patent and that said Letters Patent is hereby corrected as shown below:

Col.2, line 16: "non" should read --not--
      line 32: "may be-due" should read --may be due--
Col.3, line 36: "a1 antagonists" should read --$\alpha$1 antagonists--
Col.8, line 62: "amidopiperidine" should read --benzamidopiperidine--
Col.14, line 2: "$C_{36}H_9O_6$:HCl" should read --$C_{36}H_{39}N_3O_6$:HCl--
      line 43: "[3H]prazosin" should read --[$^3$H]prazosin--
Col.18, table 1, line 49: "Prazesin" should read --Prazosin--
      table 1, line 50: "A30380" should read --A30360--
      table 1, line 52: "6.60" should read --7.60--
Col.19, table 2, line 2: "(pK)" should read --(pK$_i$)--
      table 2, line 5: "s2b" should read "$\alpha$2b"
      table 2, line 18: "SKF-104858" should read --SKF-104856--
Col.27, line 15: "we" should read --We--

In the claims:
Claim 31, col.52, line 64: "human adrenergic" should read --human $\alpha_{1A}$ adrenergic--

Signed and Sealed this

Third Day of November, 1998

*Attest:*

BRUCE LEHMAN

*Attesting Officer*      *Commissioner of Patents and Trademarks*

UNITED STATES PATENT AND TRADEMARK OFFICE
CERTIFICATE OF CORRECTION

PATENT NO.  : 5,578,611
DATED       : November 26, 1996
INVENTOR(S) : Charles Gluchowski, Carlos C. Forray, George Chiu,
              Theresa A. Branchek, John M. Wetzel, Paul R. Hartig It is certified that error appears in the above-identified patent and that said Letters Patent is hereby corrected as shown below:

col. 16, line 37: "COS-7 cells" should read --LM(tk-) cells--

Signed and Sealed this

First Day of December, 1998

*Attest:*

BRUCE LEHMAN

*Attesting Officer*       *Commissioner of Patents and Trademarks*